United States Patent
Kaula et al.

(10) Patent No.: US 9,895,532 B2
(45) Date of Patent: Feb. 20, 2018

(54) PUDENDAL AND SACRAL NERVE STIMULATION SWEEP ALGORITHM AND METHOD

(71) Applicant: Nuvectra Corporation, Plano, TX (US)

(72) Inventors: Norbert Kaula, Arvada, CO (US); Yohannes Iyassu, Denver, CO (US)

(73) Assignee: NUVECTRA CORPORATION, Plano, TX (US)

(*) Notice: Subject to any disclaimer, the term of this patent is extended or adjusted under 35 U.S.C. 154(b) by 0 days.

(21) Appl. No.: 15/229,003

(22) Filed: Aug. 4, 2016

(65) Prior Publication Data
US 2016/0339250 A1    Nov. 24, 2016

Related U.S. Application Data

(63) Continuation of application No. 14/536,863, filed on Nov. 10, 2014, now Pat. No. 9,433,790.
(Continued)

(51) Int. Cl.
*A61N 1/36* (2006.01)
*A61N 1/05* (2006.01)
*A61N 1/372* (2006.01)

(52) U.S. Cl.
CPC .............. *A61N 1/0558* (2013.01); *A61N 1/05* (2013.01); *A61N 1/0512* (2013.01); *A61N 1/0551* (2013.01); *A61N 1/3606* (2013.01); *A61N 1/36007* (2013.01); *A61N 1/36132* (2013.01); *A61N 1/36146* (2013.01); *A61N 1/37235* (2013.01); *A61N 1/37247* (2013.01)

(58) Field of Classification Search
CPC .............. A61N 1/36107; A61N 1/0512; A61N 1/0524; A61N 1/36007
See application file for complete search history.

(56) References Cited

U.S. PATENT DOCUMENTS 5,117,840 A * 6/1992 Brennan ........... A61N 1/36007
607/138
6,533,732 B1   3/2003 Urmey
(Continued)

OTHER PUBLICATIONS

Medtronic, "Sample Operative Report-InterStim® Therapy Stage 1" 3 pages, 2014.

*Primary Examiner* — George Evanisko
(74) *Attorney, Agent, or Firm* — Haynes and Boone, LLP; Eric Li

(57) ABSTRACT

A medical system includes an implantable lead having a plurality of electrode contacts, a pulse generator coupled to the lead and configured to generate electrical pulses to be delivered to a patient through the plurality of electrode contacts, and an electronic programmer coupled to the pulse generator. The electronic programmer programs the pulse generator to generate the electrical pulses. The pulse generator is programmed to generate an electrical stimulation to be applied to the patient via one of the electrode contacts on the implantable lead. A determination is received as to whether the patient, in response to the electrical stimulation, exhibited a bellows response or a toes response. A stimulation parameter of the electrical stimulation is ramped up in response to a determination that the patient did not exhibit the bellows response or the toes response and that the patient did not feel pain in response to the electrical stimulation.

20 Claims, 27 Drawing Sheets

Related U.S. Application Data

(60) Provisional application No. 61/923,927, filed on Jan. 6, 2014, provisional application No. 61/901,499, filed on Nov. 8, 2013.

(56) References Cited

U.S. PATENT DOCUMENTS

| | | |
|---|---|---|
| 6,847,849 B2 | 1/2005 | Mamo et al. |
| 7,282,033 B2 | 10/2007 | Urmey |
| 7,699,809 B2 | 4/2010 | Urmey |
| 7,763,034 B2 | 7/2010 | Siegel et al. |
| 8,306,624 B2 | 11/2012 | Gerber et al. |
| 8,521,292 B2 | 8/2013 | Wei et al. |
| 8,886,321 B2 | 11/2014 | Rohrer et al. |
| 2008/0132979 A1 | 6/2008 | Gerber |
| 2009/0018631 A1 | 1/2009 | Snoderly |
| 2013/0072998 A1* | 3/2013 | Su ................. A61B 5/04882 607/41 |
| 2014/0243593 A1 | 8/2014 | Goode et al. |
| 2014/0257240 A1 | 9/2014 | Burdulis |
| 2015/0126894 A1* | 5/2015 | Benson ............. A61B 5/0022 600/546 |

\* cited by examiner

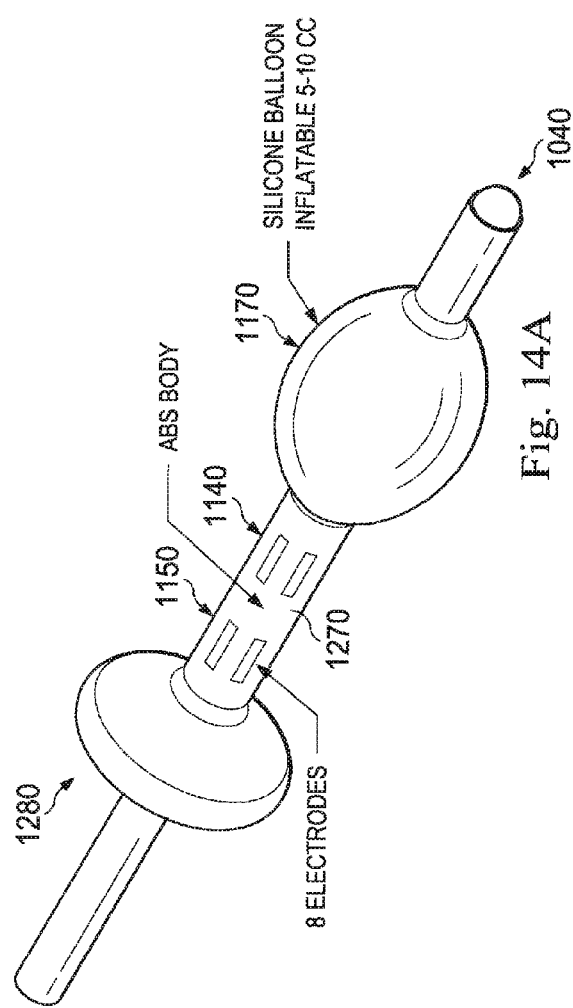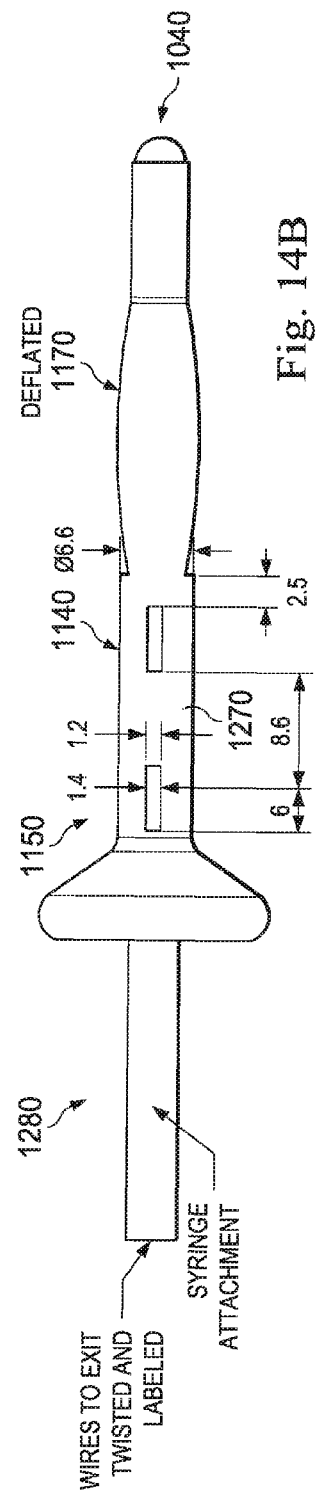

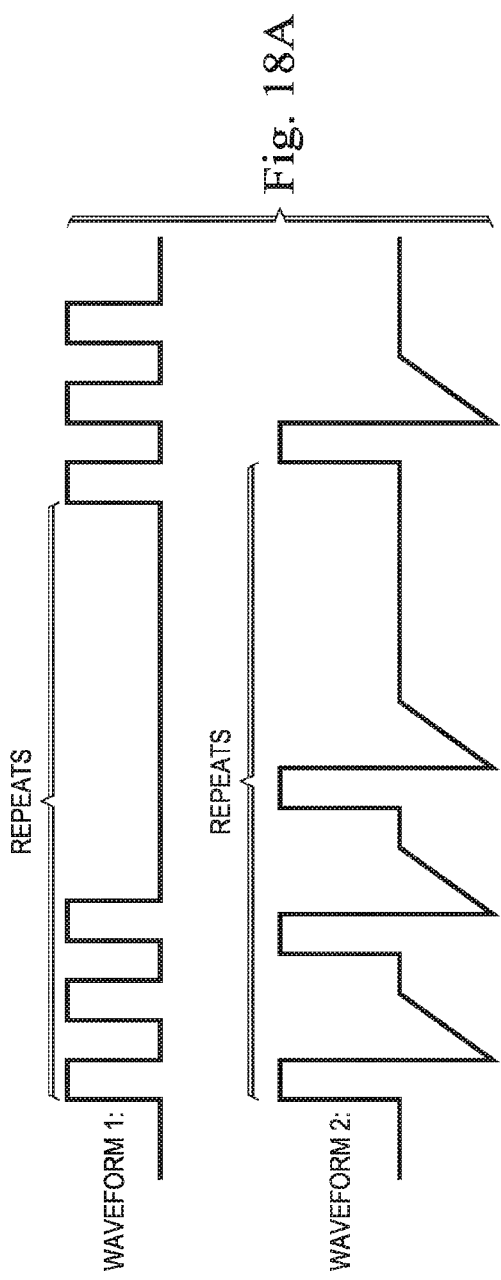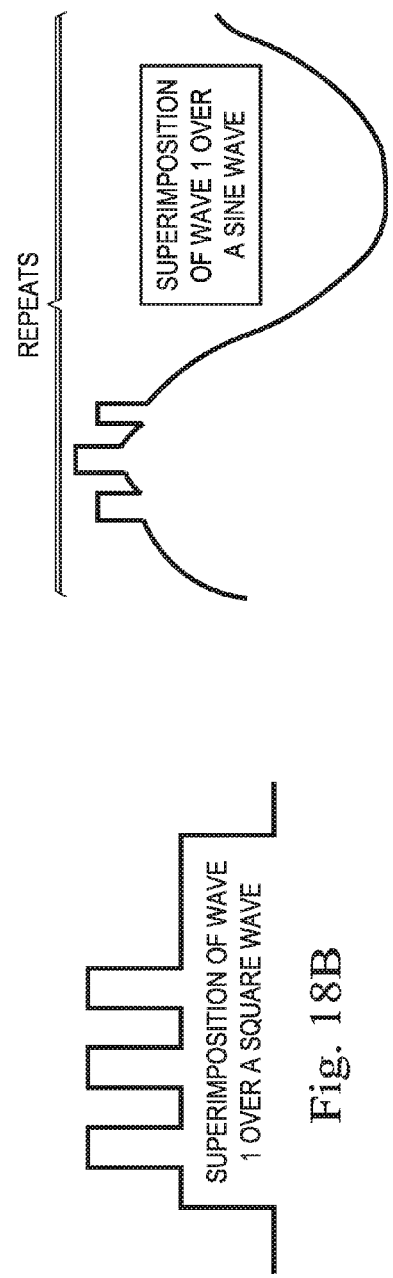

PUDENDAL AND SACRAL NERVE STIMULATION SWEEP ALGORITHM AND METHOD

PRIORITY DATA

The present application is a continuation of U.S. patent application Ser. No. 14/536,863 filed Nov. 10, 2014, which is a utility application of provisional U.S. Patent Application No. 61/901,499, filed on Nov. 8, 2013, entitled "Stimulation Apparatuses, Devices, Systems, and Methods," which is a utility application of provisional U.S. Patent Application No. 61/923,927, filed on Jan. 6, 2014, entitled "Stimulation Apparatuses, Devices, Systems, and Methods," the disclosures of each of which are hereby incorporated by reference in their respective entireties.

BACKGROUND

The invention relates to a stimulation system, such as a sacral nerve stimulation system, having a tool for programming an electrical stimulation generator, such as an implantable pulse generator (IPG), of the system.

A sacral nerve stimulator is a device used to provide electrical stimulation to the pelvic region of a patient, for example the sacral nerve or the pudendal nerve, in order to treat problems such as incontinence. The stimulator includes an implanted or external pulse generator and an implanted stimulation lead having one or more electrodes at a distal location thereof. The pulse generator provides the stimulation through the electrodes via a body portion and connector of the lead. Stimulation programming in general refers to the configuring of stimulation electrodes and stimulation parameters to treat the patient using one or more implanted leads and its attached IPG. For example, the programming is typically achieved by selecting individual electrodes and adjusting the stimulation parameters, such as the shape of the stimulation waveform, amplitude of current in mA (or amplitude of voltage in V), pulse width in microseconds, frequency in Hz, and anodic or cathodic stimulation.

Despite recent advances in medical technology, the existing sacral nerve stimulation methods, systems, and devices still have various shortcomings. For example, they may be expensive to carry out and may require too much clinician involvement. As another example, it may be difficult to know how well a stimulation lead is implanted. As another example, conventional sacral nerve stimulation systems typically require a one-to-one correspondence between stimulation channels and electrode contacts, which may be expensive and cumbersome to handle.

Therefore, although existing sacral nerve stimulators are generally adequate for their intended purposes, they have not been satisfactory in all respects.

SUMMARY

One aspect of the present disclosure involves a medical system for treating a patient. The medical system includes an implantable lead having a plurality of electrode contacts; a pulse generator coupled to the lead and configured to generate electrical pulses to be delivered to a patient through the electrode contacts; and a portable electronic programmer telecommunicatively coupled to the pulse generator. The electronic programmer programs the pulse generator to generate the electrical pulses as a part of a sacral nerve stimulation therapy for the patient. The electronic programmer includes: a graphical user interface module configured to receive input from, and display output to, a user; a memory storage module configured to store instructions; and a computer processor module configured to execute the instructions to perform the following tasks: generating, at least in part via the graphical user interface, an electronic diary in response to input from the patient who is being treated by the sacral nerve stimulation therapy, wherein the electronic diary includes a plurality of voiding responses of the patient over a period of time, and wherein the sacral nerve stimulation therapy includes electrical pulses delivered to the patient according to a first stimulation program and via a first subset of the electrode contacts on the lead; detecting, based on the voiding responses in the electronic diary, a loss of efficacy of the sacral nerve stimulation therapy; and automatically adjusting the sacral nerve stimulation therapy in response to the detected loss of efficacy, wherein the automatically adjusting of the sacral nerve stimulation therapy comprises at least one of: identifying, from a plurality of predefined stimulation programs other than the first stimulation program, a second stimulation program that best improves the efficacy of the sacral nerve stimulation therapy; and identifying, from the electrode contacts on the lead other than the first subset, a second subset of the electrode contacts that best improve the efficacy of the sacral nerve stimulation therapy.

Another aspect of the present disclosure involves a medical apparatus for treating a patient. The medical apparatus includes a computer memory module configured to store instructions; and a computer processing module configured to execute the instructions to perform the following tasks: generating, in response to input from a patient who is being treated by a sacral nerve stimulation therapy, an electronic diary that includes a plurality of voiding responses of the patient over a period of time, wherein the sacral nerve stimulation therapy includes electrical pulses delivered to the patient according to a first stimulation program and via a first subset of electrode contacts on a lead that is implanted in the patient, the lead having a plurality of electrode contacts that include the first subset; detecting, based on the voiding responses in the electronic diary, a loss of efficacy of the sacral nerve stimulation therapy; and automatically adjusting the sacral nerve stimulation therapy in response to the detected loss of efficacy, wherein the automatically adjusting of the sacral nerve stimulation therapy comprises at least one of: identifying, from a plurality of predefined stimulation programs other than the first stimulation program, a second stimulation program that best improves the efficacy of the sacral nerve stimulation therapy; and identifying, from the electrode contacts on the lead other than the first subset, a second subset of the electrode contacts that best improve the efficacy of the sacral nerve stimulation therapy.

Yet another aspect of the present disclosure involves a method of automatically adjusting a stimulation therapy to improve efficacy of the stimulation therapy. The method includes: generating, in response to input from a patient who is being treated by a sacral nerve stimulation therapy, an electronic diary that includes a plurality of voiding responses of the patient over a period of time, wherein the sacral nerve stimulation therapy includes electrical pulses delivered to the patient according to a first stimulation program and via a first subset of electrode contacts on a lead that is implanted in the patient, the lead having a plurality of electrode contacts that include the first subset; detecting, based on the voiding responses in the electronic diary, a loss of efficacy of the sacral nerve stimulation therapy; and automatically adjusting the sacral nerve stimulation therapy in response to the detected loss of efficacy, wherein the automatically adjusting of the sacral nerve stimulation therapy comprises at least one of: identifying, from a plurality of predefined stimulation programs other than the first stimulation program, a second stimulation program that best improves the efficacy of the sacral nerve stimulation therapy; and identifying, from the electrode contacts on the lead other than the first subset, a second subset of the electrode contacts that best improve the efficacy of the sacral nerve stimulation therapy.

Another aspect of the present disclosure involves a medical system of measuring a physiological feedback from a patient in response to electrical stimulation. The medical system includes: an anal electrode device that is configured to be inserted into an anal canal of a patient, wherein the anal electrode device is configured to measure a compound motor action potential (CMAP) from an anal sphincter of the patient while a sacral nerve stimulation therapy is delivered to the patient; a stimulation lead having a plurality of electrode contacts, wherein the stimulation lead is implantable inside the patient; a pulse generator electrically coupled to the stimulation lead, wherein the pulse generator is configured to generate electrical pulses of the sacral nerve stimulation therapy to be delivered by one or more of the electrode contacts to the patient; and an electronic programmer telecommunicatively coupled to the pulse generator, wherein the electronic programmer is configured to program the pulse generator to generate the electrical pulses, and wherein the electronic programmer is configured to: ramp up a stimulation parameter of the sacral nerve stimulation therapy; receive measurements of the CMAP as the stimulation parameter of the sacral nerve stimulation therapy is being ramped up; and determine a stimulation threshold based on the received measurements of the CMAP.

Yet another aspect of the present disclosure involves a method of measuring a physiological feedback from a patient in response to electrical stimulation. The method includes: ramping up a stimulation parameter of a sacral nerve stimulation therapy, wherein the sacral nerve stimulation therapy includes electrical pulses generated by a pulse generator based on programming instructions received from an electronic programmer, and wherein the electrical pulses are delivered to a patient via a stimulation lead that is implanted in the patient; measuring, via an anal electrode device that is at least partially inserted inside an anal canal of the patient, a compound motor action potential (CMAP) from an anal sphincter of the patient while the stimulation parameter of the sacral nerve stimulation therapy is being ramped up; and determining a stimulation threshold based on the measured CMAP.

Yet another aspect of the present disclosure involves an anal electrode device configured to measure a response of a patient to a stimulation pulse. The anal electrode includes: an elongate shaft that is configured to be at least partially inserted into an anal canal of the patient; a first sensory electrode disposed on a first region of the shaft, wherein the first sensory electrode is configured to measure a compound motor action potential (CMAP) from an internal sphincter of the patient while the shaft is partially inserted into the anal canal of the patient; a second sensory electrode disposed on a second region of the shaft, wherein the second sensory electrode is configured to measure the CMAP from an external sphincter of the patient while the shaft is partially inserted into the anal canal of the patient; and an inflatable balloon at a distal portion of the anal electrode device, the balloon being inflatable to inhibit removal of the anal electrode device from within the patient.

Yet another aspect of the present disclosure involves a method of generating different stimulation waveforms as a part of sacral nerve stimulation therapy. A first stimulation waveform having a first stimulation waveform characteristic is generated. The first stimulation waveform is delivered to a first body part of a patient at least in part via a first channel. A second stimulation waveform having a second stimulation waveform characteristic is generated. The second stimulation waveform characteristic is different from the first stimulation waveform characteristic. The second stimulation waveform is delivered to a second body part of the patient at least in part via a second channel that is separate and independent from the first channel. The first body part and second body part correspond to different organs or different types of nerves.

Yet another aspect of the present disclosure involves a medical system. The medical system includes an electronic programmer configured to generate programming instructions. The medical system further includes a pulse generator configured to generate, in response to the programming instructions, electrical pulses to be delivered to a patient as a part of sacral nerve stimulation therapy. The pulse generator includes: a microcontroller, a first channel, and a second channel separate and independent from the first channel. The microcontroller is configured to generate a first stimulation waveform as the electrical pulse to be outputted by the first channel, the first stimulation waveform having a first stimulation waveform characteristic. The microcontroller is configured to generate a second stimulation waveform as the electrical pulse to be outputted by the second channel, the second stimulation waveform having a second stimulation waveform characteristic different from the first stimulation waveform characteristic.

Yet another aspect of the present disclosure involves a pulse generator configured to generate electrical pulses in response to programming instructions received from an electronic programmer. The pulse generator includes: a microcontroller configured to generate a first stimulation waveform having a first frequency and a second stimulation waveform having a second frequency; a first channel configured to output the first stimulation waveform to a first electrode; and a second channel configured to output the second stimulation waveform to a second electrode, wherein the first channel and the second channel are separate and independent of each other.

Other aspects of the invention will become apparent by consideration of the detailed description and accompanying drawings.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIGS. 14A, 14B, and 14C are various diagrammatic perspective and cross-sectional views of an anal electrode device according to embodiments of the present disclosure.

FIGS. 18A-18C are example stimulation waveforms according to embodiments of the present disclosure.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
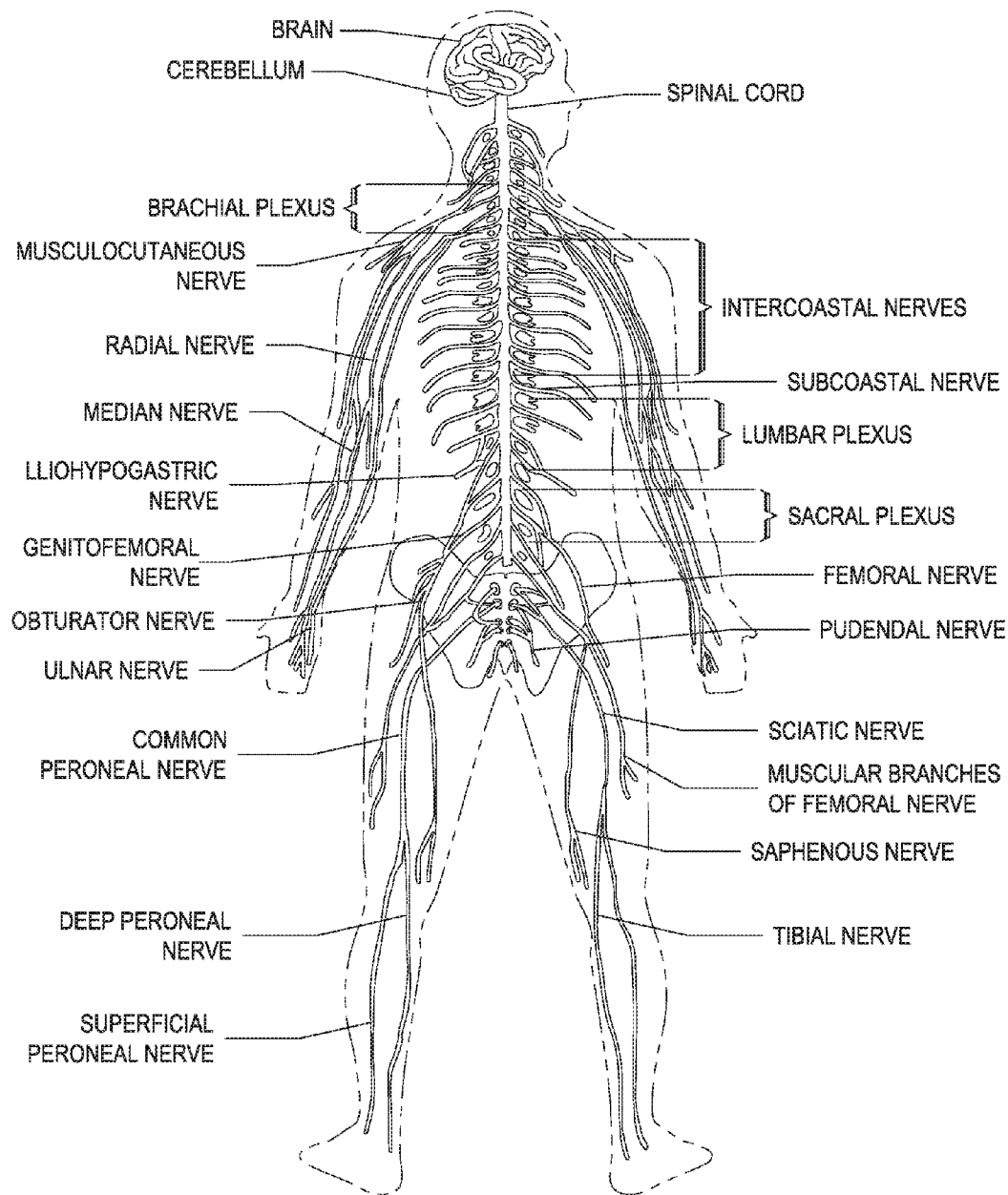
FIG. 1 is stylized overview of the human nervous system.

The human nervous system includes a complex network of neurological structures that extend throughout the body. As shown in FIG. 1, the brain interconnects with the spinal cord which branches into the brachial plexus near the shoulders and the lumbar plexus and sacral plexus in the lower back. The limb peripheral nerves of the arms extend distally from the brachial plexus down each arm. Similarly, the limb peripheral nerves of the legs extend distally from the lumbar plexus and sacral plexus. A number of the larger limb peripheral nerves are identified in FIG. 1. As discussed further below, certain aspects of the present invention are particularly well suited to stimulation of the pudendal nerves and the sacral nerves, including those identified in FIG. 1.

Figure 2B:
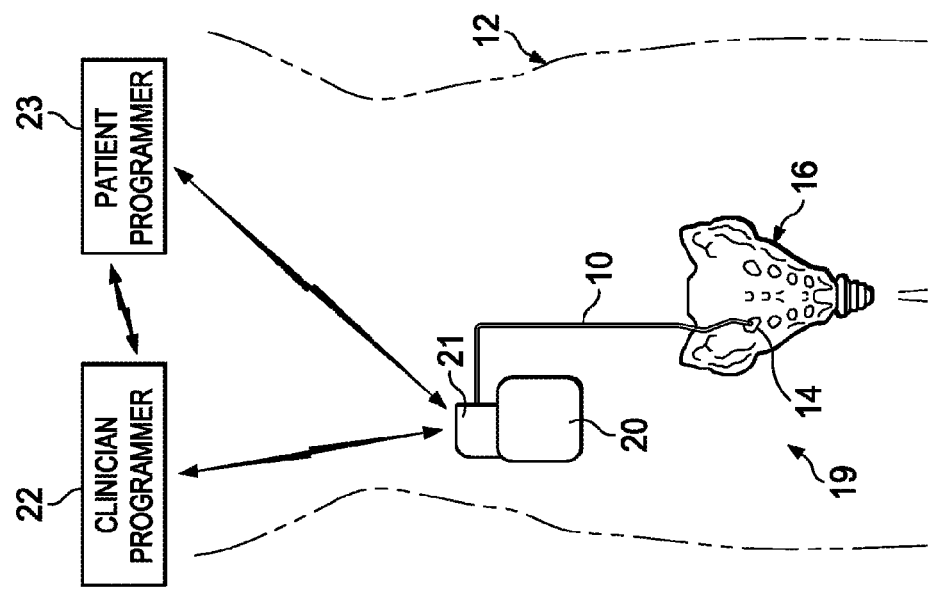
FIG. 2B is a simplified diagram illustrating an implantable neurostimulation system for stimulating nerves according to various embodiments of the present disclosure.
Figure 2A:
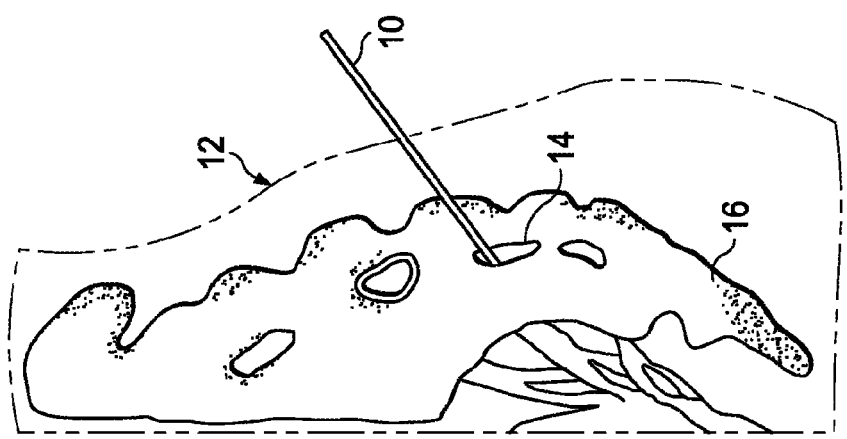
FIG. 2A is a diagram illustrating an example sacral implantation of a neurostimulation lead according to various embodiments of the present disclosure.

FIG. 2A is a simplified diagram illustrating implantation of a neurostimulation lead 10. In the example of FIG. 2A, lead 10 is inserted into body 12 of a patient, and implanted posterior to one of dorsal foramen 14 of sacrum 16. However, lead 10 alternatively may be positioned to stimulate pudendal nerves, perineal nerves, sacral spinal nerves, or other areas of the nervous system. Lead 10 may be implanted via a needle and stylet for minimal invasiveness. Positioning of lead 10 may be aided by imaging techniques, such as fluoroscopy. In some embodiments, a plurality of stimulation leads may be provided.

FIG. 2B is a diagram illustrating an implantable neurostimulation system 19 for stimulating a nerve, such as a sacral nerve, via the lead 10. Neurostimulation system 19 delivers neurostimulation to the sacral nerves or other regions of the nervous system known to treat problems including, but are not limited to: pelvic floor disorders, urinary control disorders, fecal control disorders, interstitial cystitis, sexual dysfunction, and pelvic pain. As shown in FIG. 2B, system 19 includes lead 10 and an implantable pulse generator (IPG). In addition, a proximal end of stimulation lead 10 may be coupled to a connector block 21 associated with the neurostimulator 20.

In some embodiments, the neurostimulator 20 includes an implantable pulse generator (IPG), and delivers neuro stimulation therapy to patient 12 in the form of electrical pulses generated by the IPG. In the example of FIG. 2B, the neurostimulator 20 is implanted in the upper left buttock of patient 12, but it is understood that the neurostimulator 20 be implanted at other locations in alternative embodiments.

The lead 10 carries one or more of stimulation electrodes, e.g., 1 to 8 electrodes, to permit delivery of electrical stimulation to the target nerve, such as the sacral nerve. For example, the implantable neurostimulation system 19 may stimulate organs involved in urinary, fecal or sexual function via C-fibers or sacral nerves at the second, third, and fourth sacral nerve positions, commonly referred to as S2, S3, and S4, respectively. In some embodiments, the neurostimulator 20 may be coupled to two or more leads deployed at different positions, e.g., relative to the spinal cord or sacral nerves.

The implantable neurostimulation system 19 also may include a clinician programmer 22 and a patient programmer 23. The clinician programmer 22 may be a handheld computing device that permits a clinician to program neurostimulation therapy for patient 12, e.g., using input keys and a display. For example, using clinician programmer 22, the clinician may specify neurostimulation parameters for use in delivery of neurostimulation therapy. The clinician programmer 22 supports radio frequency telemetry with neurostimulator 20 to download neurostimulation parameters and, optionally, upload operational or physiological data stored by the neurostimulator. In this manner, the clinician may periodically interrogate neurostimulator 20 to evaluate efficacy and, if necessary, modifies the stimulation parameters.

Similar to clinician programmer 22, patient programmer 23 may be a handheld computing device. The patient programmer 23 may also include a display and input keys to allow patient 12 to interact with patient programmer 23 and implantable neurostimulator 20. In this manner, the patient programmer 23 provides the patient 12 with an interface for control of neurostimulation therapy by neurostimulator 20. For example, the patient 12 may use patient programmer 23 to start, stop or adjust neurostimulation therapy. In particular, the patient programmer 23 may permit the patient 12 to adjust stimulation parameters such as duration, amplitude, pulse width and pulse rate, within an adjustment range specified by the clinician via the clinician programmer 22.

The neurostimulator 20, clinician programmer 22, and patient programmer 23 may communicate via wireless communication, as shown in FIG. 2B. The clinician programmer 22 and patient programmer 23 may, for example, communicate via wireless communication with neurostimulator 20 using RF telemetry techniques known in the art. The clinician programmer 22 and patient programmer 23 also may communicate with each other using any of a variety of local wireless communication techniques, such as RF communication according to the 802.11 or Bluetooth specification sets, or other standard or proprietary telemetry protocols. It is also understood that although FIG. 2B illustrates the patient programmer 22 and the clinician programmer 23 as two separate devices, they may be integrated into a single programmer in some embodiments.

Figure 3A:
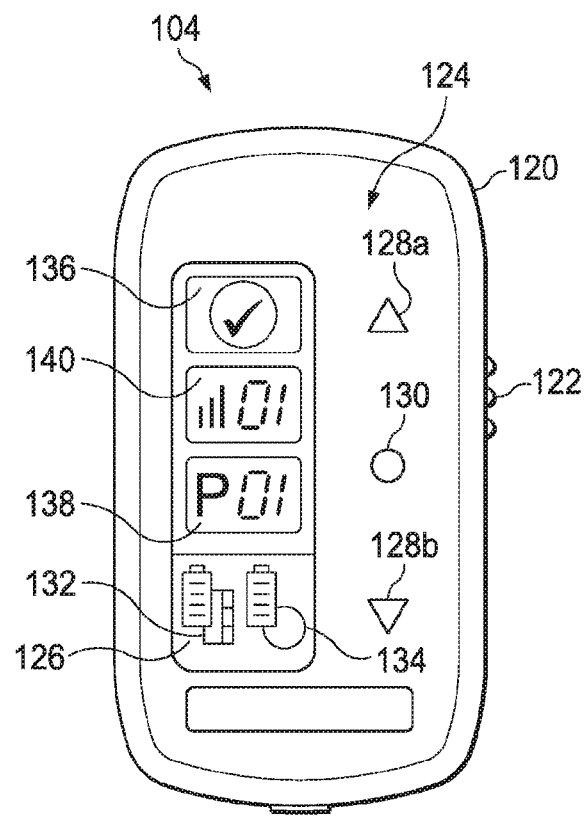
FIGS. 3A-3B illustrate an example pocket controller in accordance with one embodiment of the present disclosure.
Figure 3B:
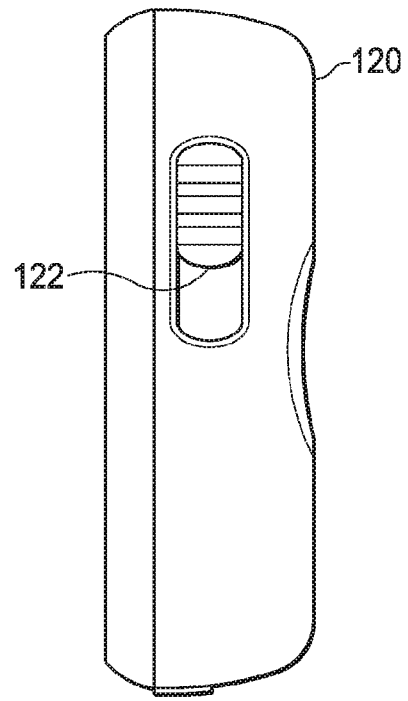
Figure 4:
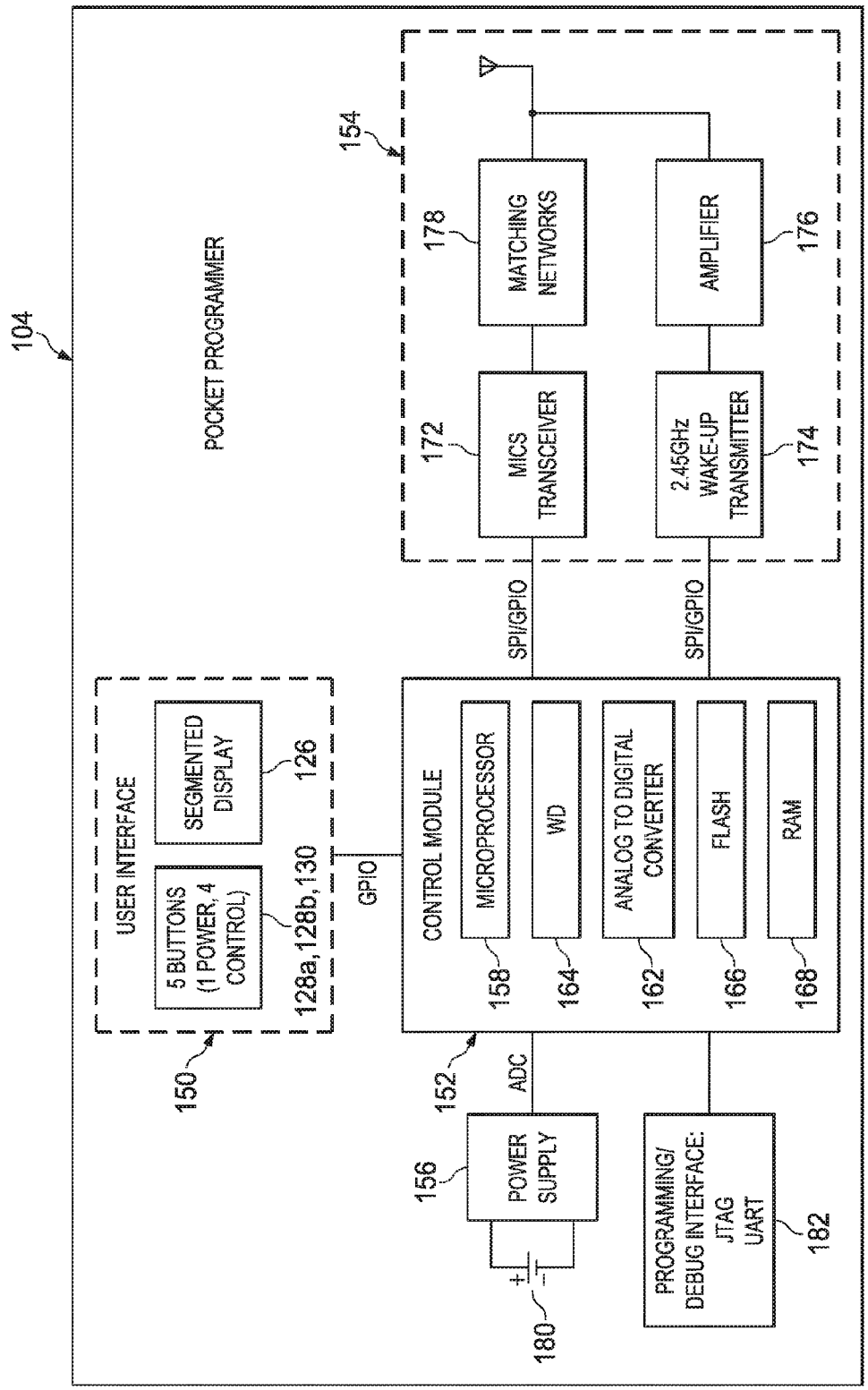
FIG. 4 is a block diagram of components of the example pocket controller of FIGS. 3A-3B in accordance with one embodiment of the present disclosure.
Figure 5A:
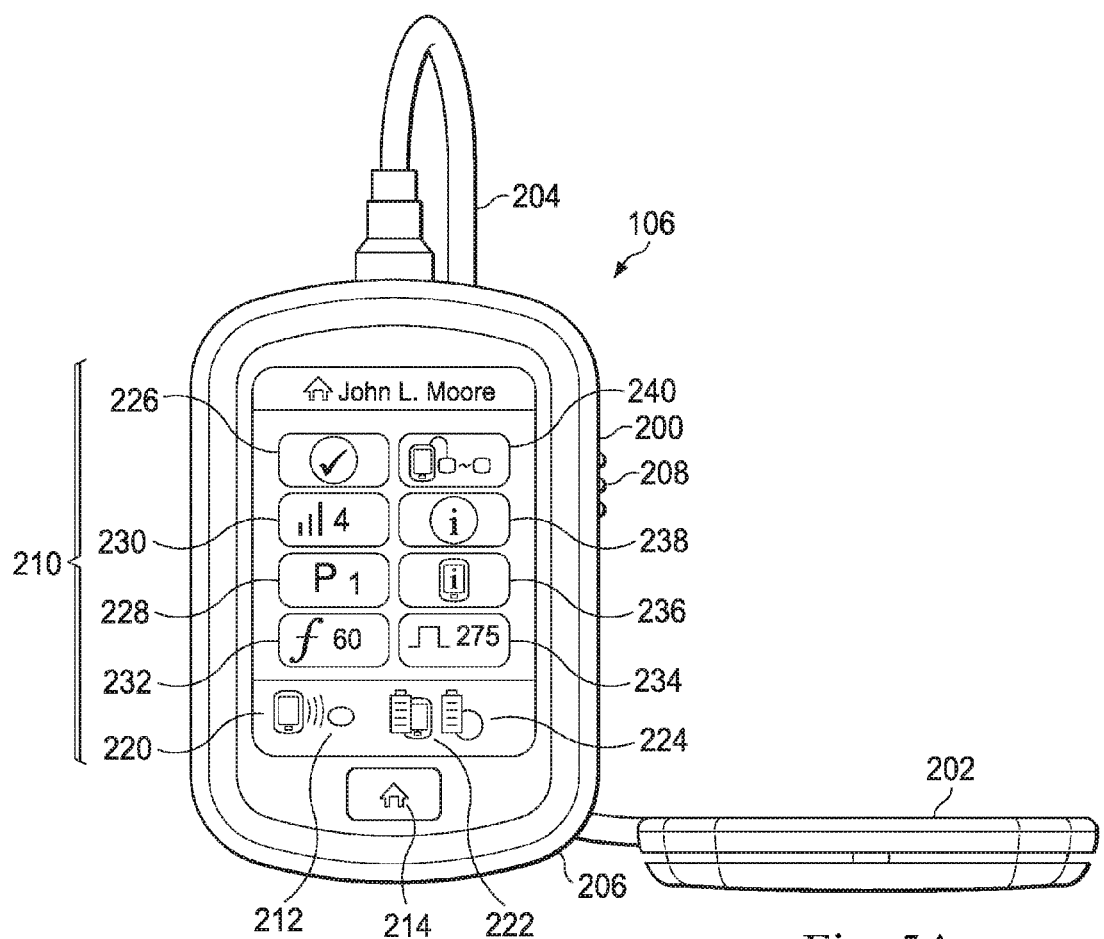
FIGS. 5A-5B illustrate an example patient controller charger in accordance with one embodiment of the present disclosure.
Figure 5B:
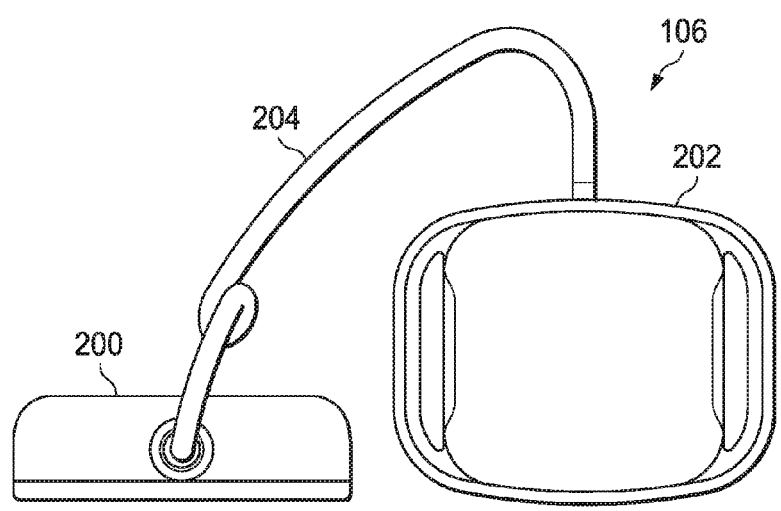
Figure 6:
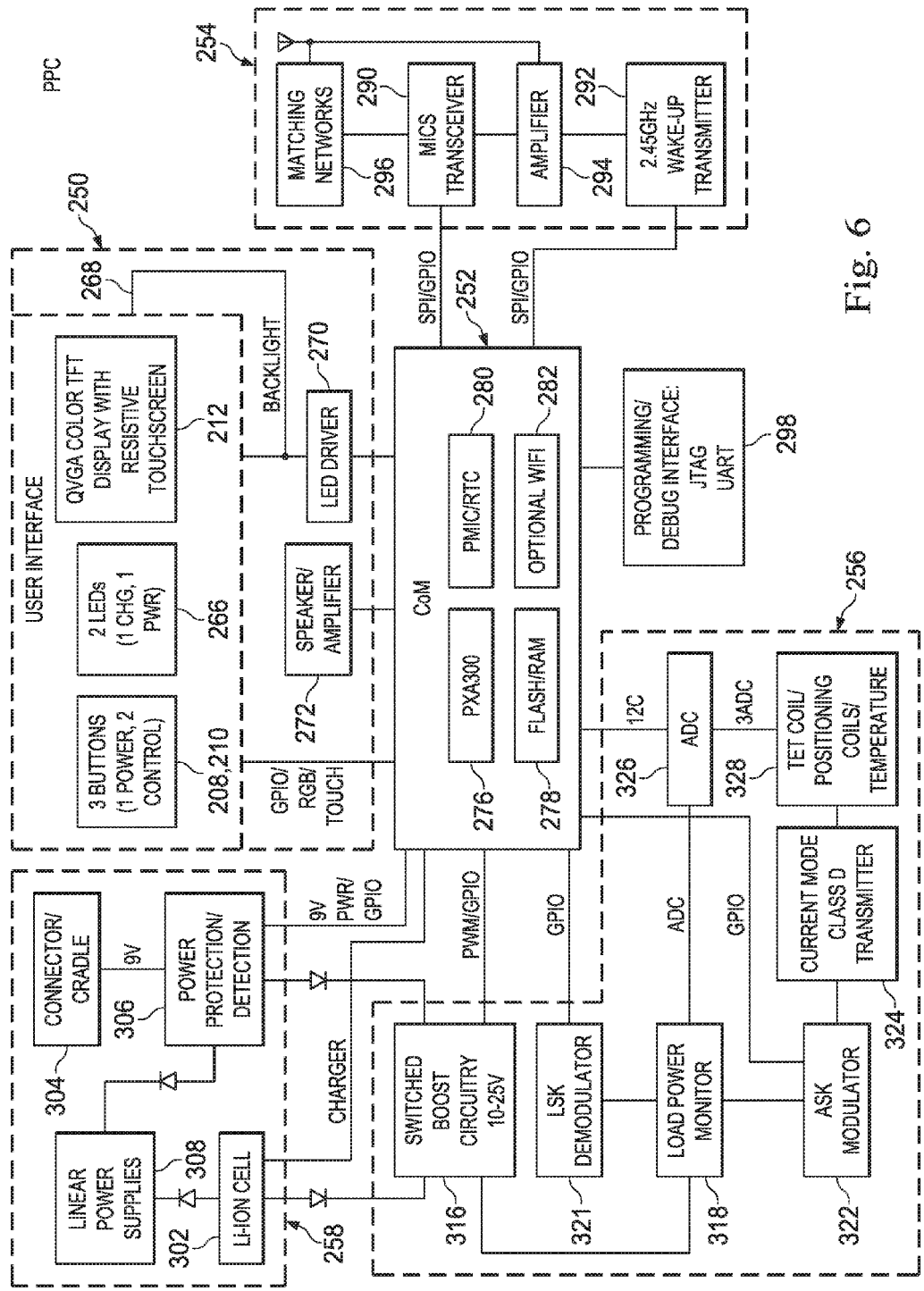
FIG. 6 is a block diagram of components of the example patient controller charger of FIGS. 5A-5B in accordance with one embodiment of the present disclosure.

FIGS. 3A-3B, 4, 5A-5B, and 6 illustrate various example embodiments of the patient programmer 22 according to various aspects of the present disclosure. In more detail, FIGS. 3A-3B and 4 are directed to a patient programmer that is implemented as a pocket controller 104, and FIGS. 5A-5B and 6 are directed to a patient programmer that is implemented as a patient programmer charger (PPC) 106.

Referring now to FIGS. 3A and 3B, the pocket controller 104 comprises an outer housing 120 having an on-off switch 122, a user interface comprising a plurality of control buttons 124, and a display 126. In this embodiment, the housing 120 is sized for discreetness and may be sized to fit easily in a pocket and may be about the same size as a key fob. In one example, the housing 120 forming the pocket controller 104 has a thickness of less than about 1.5 inch, a width of less than about 1.5 inch, and a height of less than about 3 inches. In another example, the housing 120 forming the pocket controller 104 has a thickness of about 0.8 inch, a width of about 1.4 inch, and a height of about 2.56 inch. However, both larger and smaller sizes are contemplated.

In this example, the control buttons 124 include two adjustment buttons 128*a*, 128*b*, a select button 130, and an emergency off button (not shown, but disposed on a side of the housing 120 opposing the on-off switch 122). The two adjustment buttons 128*a*, 128*b* allow a user to scroll or highlight available options and increase or decrease values shown on the display 126. The select button 130 allows a user to enter the value or select the highlighted options to be adjusted by actuation of the adjustment buttons 128*a*, 128*b*. In this example, the buttons 128*a*, 128*b* are used to navigate to one of the three available functions: 1) electrical stimulation on/off, 2) control stimulation amplitude adjustment, and 3) electrical stimulation program selection. Once the desired function is highlighted, the select button is pushed to allow changes (i.e. change the stimulation amplitude, select a different stimulation program, or turn the electrical stimulation on or off). In some examples, the IPG control functions of the pocket controller 104 consist of these functions. The emergency off button is disposed for easy access for a patient to turn off stimulation from the IPG 102 if the IPG provides too much stimulation or stimulation becomes uncomfortable for the patient. Allowing the user to scroll through the plurality of options (also referred to herein as operational parameters) that can be adjusted via the pocket controller 104 provides the user the confidence to carry only the pocket controller 104 while away from home. Users may be reluctant to carry only a conventional controller that allows adjustment of only a single operational parameter out of fear that they may need to adjust a different operational parameter while away from a more full-featured controller.

In the embodiment shown, the display 126 is an LCD display arranged to convey information to the user regarding selectable options, present settings, operating parameters and other information about the IPG 102 or the pocket controller 104. In this example, the display 126 shows the pocket controller's battery status at 132, the IPG's battery status at 134, the IPG's on or off status at 136, the currently selected electrical stimulation program at 138, and the amplitude setting of the running electrical stimulation program at 140. Other types of displays are also contemplated.

FIG. 4 shows a block diagram of components making up the pocket controller 104. It includes a user interface 150, a control module 152, a communication module 154, and a power storing controller 156. The user interface 150 is comprised of the buttons 128*a*, 128*b*, 130 and the display 126 described above with reference to FIG. 3A.

As can be seen, the user interface 150 is in communication with the control module 152. The control module 152 comprises a processor 158, memory, an analog-digital converter 162, and a watch dog circuit 164. The processor 158 may include a microprocessor, a controller, a digital signal processor (DSP), an application specific integrated circuit (ASIC), a field programmable gate array (FPGA), discrete logic circuitry, or the like. The processor 158 is configured to execute code or instructions provided in the memory. Here, the memory is comprised of flash memory 166 and RAM memory 168. However, the memory may include any volatile or non-volatile media, such as a random access memory (RAM), read only memory (ROM), non-volatile RAM (NVRAM), electrically erasable programmable ROM (EEPROM), flash memory, and the like. In some embodiments, the memory stores sets of stimulation control parameters that are available to be selected for delivery through the communication module 154 to the IPG 102 for electrical stimulation therapy. The AD converter 162 performs known functions of converting signals and the WD 164 is arranged to time out when necessary, such as in an event where the software becomes stuck in a loop. In one embodiment, the control module 152 comprises integrated circuits disposed on a PC board.

The communication module 154 comprises a medical implant communication service (MICS) RF transceiver 172 used to communicate with the IPG 102 to communicate desired changes and to receive status updates from and relating to the IPG 102, such as battery status and any error information. As used herein, MICS refers to wireless communications in a frequency band ranging from about 402 MHz to about 405 MHz, which is dedicated for communications with implanted medical devices. In this example, the MICS RF transceiver 172 utilizes a loop antenna for the communications with the IPG 102. Other antennas, such as, for example, dipole, chip antennas, or other known in the art also may be used. The communication module 154 also includes a wake up transmitter 174, an amplifier 176, and matching networks 178. The wake up transmitter 174 operates on a high frequency and is configured to send a short signal burst to wake up the IPG 102 when it is in a power-saving mode. Once the IPG 102 is ready, a communications link can be established between the IPG 102 and pocket controller 104, and communications can then occur over the MICS transceiver 172 using a standard frequency for a medical device transmission. The matching networks 178 tunes the antenna for optimum transmission power for the frequency selected. The pocket controller 104 also includes a programming interface 182. This may be used during manufacturing to load an operating system and program the pocket controller 104.

The power storing controller 156 is configured to convert power to recharge one or more rechargeable batteries 180. The batteries 180 provide power to operate the pocket controller 104 allowing it to receive user inputs and transmit control signals to the IPG 102. Some embodiments use primary cell batteries instead of rechargeable batteries. As indicated above, this pocket controller 104 is part of a larger system that contains the PPC 106 with a rich feature set for controlling the IPG 102 and includes an integrated battery charger used to charge the IPG's battery. By providing both the pocket controller 104 and the PPC 106, the patient can have a small unobtrusive device to carry around as they go about their daily business and a larger more full featured device which they can use in the comfort and privacy of their homes.

The pocket controller 104 is not only comfortable to carry in a pocket, but can also be attached to a key ring, lanyard, or other such carrying device for ease of daily use. Its functions are a subset of functions found on the PPC 106, and permit a user to power stimulation from the IPG on and off (i.e., the IPG 102 remains on, but stimulation is toggled between the on state when the IPG 102 is emitting electrical pulses and the off state when the IPG 102 is not emitting electrical pulses but remains in the standby mode for additional communications from the pocket controller 104, the PPC 106, or both), select which electrical stimulation program to run, and globally adjust the amplitude of electrical pulses emitted in a series of electrical pulses emitted by the IPG 102. By limiting the functions of the pocket controller to those most commonly used on a daily basis, the device becomes much less intimidating to the patient, and allows it to be kept very small. By keeping the device small, such as about key fob size, it becomes unobtrusive and the patient is more comfortable with having and using an implanted device.

FIGS. 5A-5B show the PPC 106 in greater detail. FIG. 5A is a front view of the PPC and FIG. 5B is a top view of FIG. 5A. The PPC 106 performs all the same operating functions as the pocket controller 104, but includes additional operating functions making it a multi-function full-featured, advanced patient controller charger. In the embodiment shown, the PPC 106 provides a simple but rich feature set to the more advanced user, along with the charging functions.

The PPC 106 includes a controller-charger portion 200 and a coil portion 202 connected by a flexible cable 204 and sharing components as described below. The controller-charger portion 200 comprises an outer housing 206 having an on-off switch 208 on its side, a plurality of control buttons 210, and a display 212, and an emergency off button (not shown, but disposed on a side of the housing 206 opposing the on-off switch 208). In this embodiment, the control buttons 210 are icons on the display 212, and the display is a full color, touch screen, graphical user interface. In addition, the controller-charger portion 200 includes a home button 214 configured to return the displayed images to a home screen. The controller-charger portion 200 is larger than the pocket controller 104 and in one embodiment is sized with a height greater than about 3 inches, a width greater than about 2.5 inches, and a thickness greater than about 0.8 inch. In another embodiment, the controller-charger portion is sized with a width of about 3.1 inches, a height of about 4.5 inches, and thickness of about 0.96 inches, although both larger and smaller sizes are contemplated.

In this example, the control buttons 210 allow a user to select a desired feature for control or further display. Particularly, the control buttons 210 enable functions of the PPC 106 that are the same as those of the pocket controller 104 (stimulation on/off, program stimulation amplitude adjustment, and stimulation program selection) along with additional features including: charging IPG battery, individual pulse stimulation amplitude adjustment that adjusts an amplitude of an individual pulse relative to the amplitude of an adjacent pulse in a series of pulses emitted by the IPG 102, stimulation program frequency adjustment, individual pulse width adjustment, detailed IPG status, detailed PPC status, PPC setup/configuration, a PPC battery status indicator, PPC to IPG communication status indicator, and other items and functions. The detailed IPG status may include, for example, IPG serial number and IPG software revision level. Detailed PPC status may include, for example, date and time setting, brightness control, audio volume and mute control, and PPC serial number and software revision level.

By having a pocket controller 104 that is limited to a plurality, such as only three controls (stimulation on/off, program amplitude adjust, and stimulation program selection), for example, a user can quickly and easily identify and select the features that are most commonly used. Features that are used less frequently, such as IPG recharge, are included on the full-featured PPC, but not the pocket controller 104. Features that are seldom accessed, or not accessed at all by some users, including individual pulse amplitude adjust, pulse width adjust, stimulation program frequency adjust, or serial number and software revision information, are also not included on the limited-feature pocket controller, but are included on the PPC. This allows the pocket controller to be significantly smaller, with a very simple and easy to user interface, as compared to systems that need to support all of these features.

Referring to the example shown in FIG. 5A, the touch screen display 212 is arranged to convey information to the user regarding selectable options, current settings, operating parameters and other information about the IPG 102 or the PPC 106. In this example, the display 212 shows a MICS communication indicator 220, the PPC's battery status at 222, the IPG's battery status at 224, the IPG's on or off status at 226, the currently selected electrical stimulation program at 228, and the amplitude setting of the active electrical stimulation program at 230. In addition, the display 212 shows the frequency 232, the pulse width setting 234, a selectable status icon for accessing detailed PPC information 236, a selectable status icon for accessing detailed IPG information 238, and a selectable icon for enabling IPG charging 240. Selecting any single icon may activate another menu within that selected subject area. The controller-charger portion 200 may include a rechargeable battery whose charge status is shown by the PPC's battery status at 222.

The coil portion 202 is configured to wirelessly charge the batteries in the IPG 102. In use, the coil portion 202 is applied against the patient's skin or clothing externally so that energy can be inductively transmitted and stored in the IPG battery. As noted above, the coil portion 202 is connected with the integrated controller-charger portion 200. Accordingly, the controller-charger portion 200 can simultaneously display the current status of the coil portion 204, the battery power level of the IPG 102, as well as the battery power level of the PPC. Accordingly, controlling and charging can occur in a more simplistic, time-effective manner, where the patient can perform all IPG maintenance in a single sitting. In addition, since the most commonly used features of the PPC 106 are already functional on the pocket controller, the PPC 106 may be left at home when the user does not desire to carry the larger, more bulky PPC.

FIG. 6 shows a block diagram of the components making up the PPC 106. It includes a user interface 250, a control module 252, a communication module 254, an IPG power charging module 256, and a power storing module 258. The user interface 250 is comprised of the buttons 210 and the display 212 described above. In this embodiment however, the user interface 250 also includes one or more LEDs 266 signifying whether the PPC 106 is charging or powered on and a backlight 268 that illuminates the color display. In some embodiments, these LEDs may have colors symbolizing the occurring function. An LED driver 270 and a speaker or amplifier 272 also form a part of the user interface 250.

As can be seen, the user interface 250 is in communication with the control module 252. The control module 252 comprises a processor 276, memory 278, and a power management integrated circuit (PMIC)/real time clock (RTC) 280. In the example shown, the control module 252 also includes a Wi-Fi RF transceiver 282 that allows the PPC 106 to connect to a wireless network for data transfer. For example, it may permit doctor-patient interaction via the internet, remote access to PPC log files, remote diagnostics, and other information transfer functions. The PMIC 280 is configured to control the charging aspects of the PPC 106. The Wi-Fi transceiver 282 enables Wi-Fi data transfer for programming the PPC 106, and may permit wireless access to stored data and operating parameters. Some embodiments also include a Bluetooth RF transceiver for communication with, for example, a Bluetooth enabled printer, a keyboard, etc.

In one embodiment, the control module 252 also includes an AD converter and a watch dog circuit as described above with reference to the control module 252. Here, the memory 278 is comprised of flash memory and RAM memory, but may be other memory as described above. In some embodiments, the processor 276 is an embedded processor running a WinCE operating system (or any real time OS) with the graphics interface 250, and the memory 278 stores sets of stimulation control parameters that are available to be selected for delivery through the communication module 254 to the IPG 102 for electrical stimulation therapy. In one embodiment, the control module 252 comprises integrated circuits disposed on a PC board.

The communication module 254 comprises a MICS RF transceiver 290, a wake up transmitter 292, an amplifier 294, and matching networks 296. The communication module 254 may be similar to the communication module 154 discussed above, and will not be further described here. The PPC 206 also includes a programming interface 298 that may be used during manufacturing to load an operating system and program the PPC 206.

The power storing module 258 is configured to convert power to recharge one or more rechargeable batteries 302. In this embodiment, the batteries 302 are lithium-ion cells that provide power to operate the PPC 106 allowing it to receive user inputs, transmit control signals to, and charge the IPG 102. The power storing module 258 includes a connector 304 for connecting to a power source, a power protection detection circuit 306 for protecting the PPC from power surges, and linear power supplies 308 for assisting with the electric transfer to charge the batteries 302. As can be seen, the control module 252 aids with the charging and is configured to monitor and send the battery charge level to the user interface 250 for display. The connector 304 connects the PPC, directly or indirectly, to a power source (not shown) such as a conventional wall outlet for receiving electrical current. In some embodiments, the connector 304 comprises a cradle.

The power charging module 256 communicates with the control module 252 and is arranged to magnetically or inductively charge the IPG 102. In the embodiments shown, it is magnetically or inductively coupled to the IPG 102 to charge rechargeable batteries on the IPG 102. The charging module 256 includes components in both the controller-charger portion 200 and the coil portion 202 (FIGS. 5A-5B). It includes switch boost circuitry 316, a load power monitor 318, an LSK demodulator 321, a ASK modulator 322, a current mode transmitter 324, an ADC 326, and coils 328. As can be seen, the control module 252 aids with the charging and is configured to monitor and send the IPG battery charge level to the user interface 250 for display.

In this embodiment, the coils 328 are disposed in the coil portion 202 and are configured to create magnetic or inductive coupling with components in the IPG 102. Since the coil portion 202 is integrated with the controller-charger portion 200, both operate from a single battery 302. Accordingly, as can be seen by the circuitry, the battery 302 powers the control module 252 and all its associated components. In addition, the battery 302 powers the power charging module 256 for recharging the IPG 102.

Because the coil portion 202 is integrated with the controller-charger portion 200, the control module 252 provides a single control interface and a single user interface for performing both functions of controlling the IPG 102 and of charging the IPG 102. In addition, because the controller-charger portion 200 and the coil portion 202 are integrated, the controller-charger portion 200 simultaneously controls both the current status of the charger, the battery power level of the IPG 102, as well as the battery power level of the PPC. Accordingly, controlling and charging can occur in a more simplistic, time-effective manner, where the patient can perform all IPG maintenance in a single sitting. In addition, since the most commonly used features of the PPC 106 are already functional on the pocket controller, the PPC 106 may be left at home when the user does not desire to carry the larger, more bulky PPC.

Figure 7:
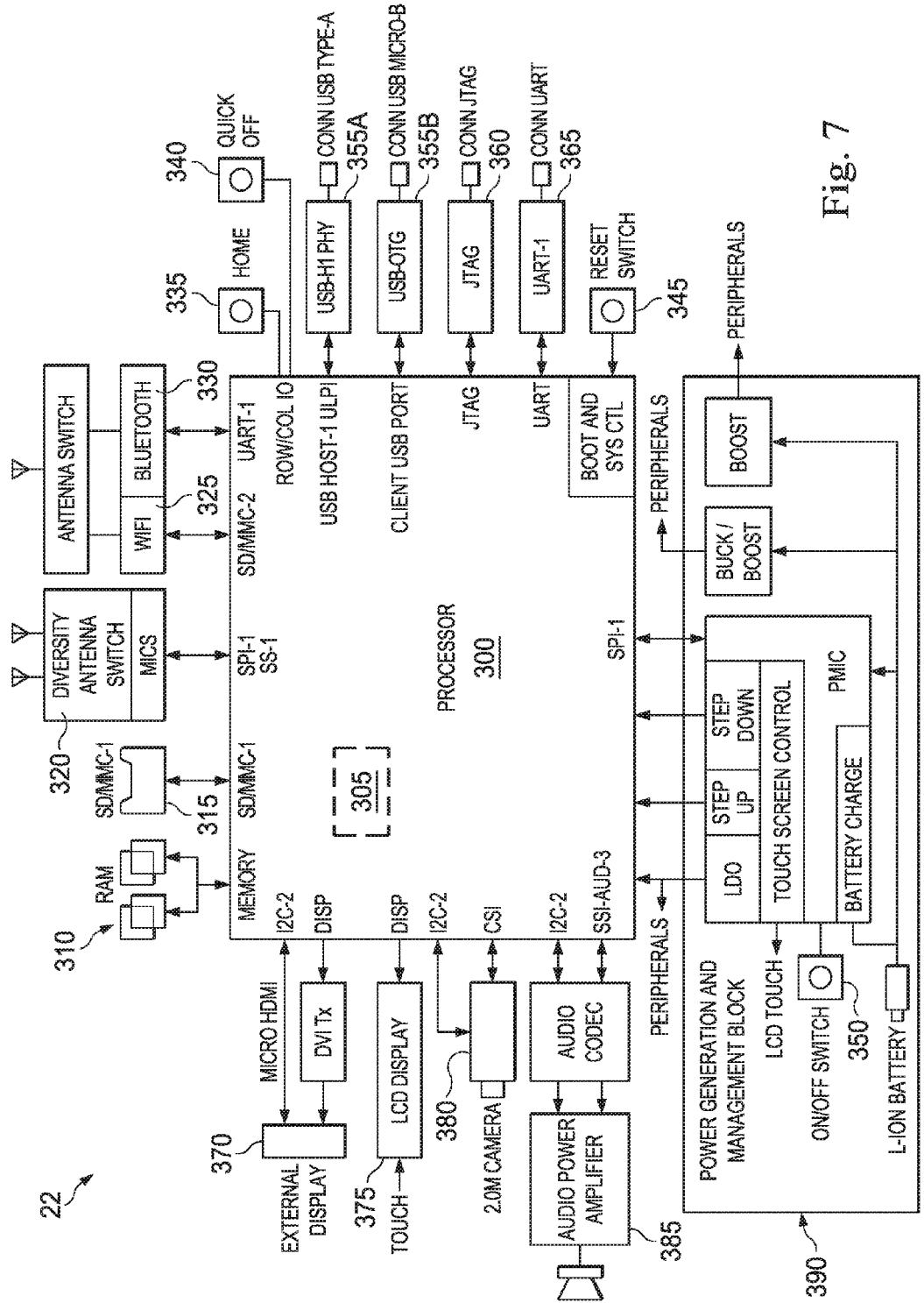
FIG. 7 is a block diagram of a clinician programmer according to one embodiment of the present disclosure.

FIG. 7 shows a block diagram of one example embodiment of a clinician programmer (CP), for example the CP 22 shown in FIG. 2B. The CP 22 includes a printed circuit board ("PCB") that is populated with a plurality of electrical and electronic components that provide power, operational control, and protection to the CP 22. With reference to FIG. 7, the CP includes a processor 300. The processor 300 is a controller for controlling the CP 22 and, indirectly, the IPG 20 as discussed further below. In one construction, the processor 300 is an applications processor model i.MX515 available from Freescale Semiconductor. More specifically, the i.MX515 applications processor has internal instruction and data cashes, multimedia capabilities, external memory interfacing, and interfacing flexibility. Further information regarding the i.MX515 applications processor can be found in, for example, the "IMX510EC, Rev. 4" data sheet; dated August 2010; published by Freescale Semiconductor at www.freescale.com, the content of the data sheet being incorporated herein by reference. Of course, other processing units, such as other microprocessors, microcontrollers, digital signal processors, etc., can be used in place of the processor 300.

The CP 22 includes memory, which can be internal to the processor 300 (e.g., memory 305), external to the processor 300 (e.g., memory 310), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 300 executes software that is capable of being stored in the RAM (e.g., during execution), the ROM (e.g., on a generally permanent basis), or another non-transitory computer readable medium such as another memory or a disc. The CP 22 also includes input/output ("I/O") systems that include routines for transferring information between components within the processor 300 and other components of the CP 22 or external to the CP 22.

Software included in the implementation of the CP 22 is stored in the memory 305 of the processor 300, RAM 310, ROM 315, or external to the CP 22. The software includes, for example, firmware, one or more applications, program data, one or more program modules, and other executable instructions. The processor 300 is configured to retrieve from memory and execute, among other things, instructions related to the control processes and methods described below for the CP 22. For example, the processor 300 is configured to execute instructions retrieved from the memory 140 for establishing a protocol to control the IPG 20.

One memory shown in FIG. 7 is memory 310, which can be a double data rate (DDR2) synchronous dynamic random access memory (SDRAM) for storing data relating to and captured during the operation of the CP 22. In addition, a secure digital (SD) multimedia card (MMC) can be coupled to the CP for transferring data from the CP to the memory card via slot 315. Of course, other types of data storage devices can be used in place of the data storage devices shown in FIG. 7.

The CP 22 includes multiple bi-directional radio communication capabilities. Specific wireless portions included with the CP 22 are a Medical Implant Communication Service (MICS) bi-direction radio communication portion 320, a WiFi bi-direction radio communication portion 325, and a Bluetooth bi-direction radio communication portion 330. The MICS portion 320 includes a MICS communication interface, an antenna switch, and a related antenna, all of which allows wireless communication using the MICS specification. The WiFi portion 375 and Bluetooth portion 330 include a WiFi communication interface, a Bluetooth communication interface, an antenna switch, and a related antenna all of which allows wireless communication following the WiFi Alliance standard and Bluetooth Special Interest Group standard. Of course, other wireless local area network (WLAN) standards and wireless personal area networks (WPAN) standards can be used with the CP 22.

The CP 22 includes three hard buttons: a "home" button 335 for returning the CP to a home screen for the device, a "quick off" button 340 for quickly deactivating stimulation IPG, and a "reset" button 345 for rebooting the CP 22. The CP 22 also includes an "ON/OFF" switch 350, which is part of the power generation and management block (discussed below).

The CP 22 includes multiple communication portions for wired communication. Exemplary circuitry and ports for receiving a wired connector include a portion and related port for supporting universal serial bus (USB) connectivity 355, including a Type-A port and a Micro-B port; a portion and related port for supporting Joint Test Action Group (JTAG) connectivity 360, and a portion and related port for supporting universal asynchronous receiver/transmitter (UART) connectivity 365. Of course, other wired communication standards and connectivity can be used with or in place of the types shown in FIG. 7.

Another device connectable to the CP 22, and therefore supported by the CP 22, is an external display. The connection to the external display can be made via a micro High-Definition Multimedia Interface (HDMI) 370, which provides a compact audio/video interface for transmitting uncompressed digital data to the external display. The use of the HDMI connection 370 allows the CP 22 to transmit video (and audio) communication to an external display. This may be beneficial in situations where others (e.g., the surgeon) may want to view the information being viewed by the healthcare professional. The surgeon typically has no visual access to the CP 22 in the operating room unless an external screen is provided. The HDMI connection 370 allows the surgeon to view information from the CP 22, thereby allowing greater communication between the clinician and the surgeon. For a specific example, the HDMI connection 370 can broadcast a high definition television signal that allows the surgeon to view the same information that is shown on the LCD (discussed below) of the CP 22.

The CP 22 includes a touch screen I/O device 375 for providing a user interface with the clinician. The touch screen display 375 can be a liquid crystal display (LCD) having a resistive, capacitive, or similar touch-screen technology. It is envisioned that multitouch capabilities can be used with the touch screen display 375 depending on the type of technology used.

The CP 22 includes a camera 380 allowing the device to take pictures or video. The resulting image files can be used to document a procedure or an aspect of the procedure. For example, the camera 380 can be used to take pictures of barcodes associated with the IPG 20 or the leads 120, or documenting an aspect of the procedure, such as the positioning of the leads. Similarly, it is envisioned that the CP 22 can communicate with a fluoroscope or similar device to provide further documentation of the procedure. Other devices can be coupled to the CP 22 to provide further information, such as scanners or RFID detection. Similarly, the CP 22 includes an audio portion 385 having an audio codec circuit, audio power amplifier, and related speaker for providing audio communication to the user, such as the clinician or the surgeon.

The CP 22 further includes a power generation and management block 390. The power block 390 has a power source (e.g., a lithium-ion battery) and a power supply for providing multiple power voltages to the processor, LCD touch screen, and peripherals.

Figure 8:
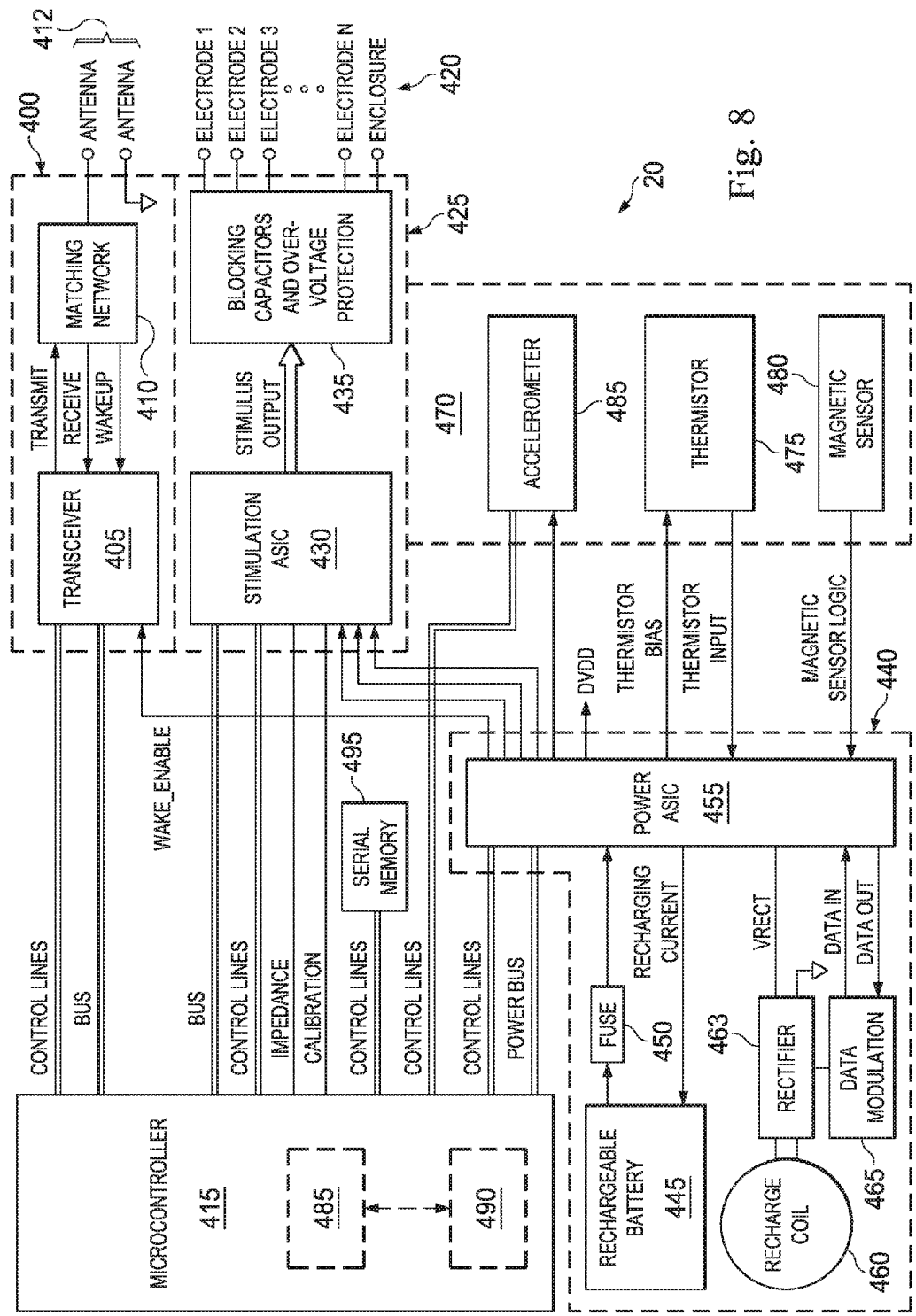
FIG. 8 is a block diagram of an implantable pulse generator according to one embodiment of the present disclosure.

FIG. 8 shows a block diagram of an example embodiment of an IPG, for example an embodiment of the IPG 20 shown in FIG. 2B. The IPG 20 includes a printed circuit board ("PCB") that is populated with a plurality of electrical and electronic components that provide power, operational control, and protection to the IPG 20. With reference to FIG. 8, the IPG 20 includes a communication portion 400 having a transceiver 405, a matching network 410, and antenna 412. The communication portion 400 receives power from a power ASIC (discussed below), and communicates information to/from the microcontroller 415 and a device (e.g., the CP 22) external to the IPG 20. For example, the IPG 20 can provide bi-direction radio communication capabilities, including Medical Implant Communication Service (MICS) bi-direction radio communication following the MICS specification.

The IPG 20, as previously discussed, provides stimuli to electrodes 150 of an implanted medical electrical lead 110. As shown in FIG. 8, N electrodes 150 are connected to the IPG 20. In addition, the enclosure or housing 420 of the IPG 20 can act as an electrode. The stimuli are provided by a stimulation portion 425 in response to commands from the microcontroller 415. The stimulation portion 425 includes a stimulation application specific integrated circuit (ASIC) 430 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, Flash, etc. The stimulation ASIC 430 can include a processor, memory, and firmware for storing preset pulses and protocols that can be selected via the microcontroller 415. The providing of the pulses to the electrodes 150 is controlled through the use of a waveform generator and amplitude multiplier of the stimulation ASIC 430, and the blocking capacitors and overvoltage protection circuitry of the stimulation portion 425, as is known in the art. The stimulation portion 425 of the IPG 20 receives power from the power ASIC (discussed below). The stimulation ASIC 430 also provides signals to the microcontroller 415. More specifically, the stimulation ASIC 430 can provide impedance values for the channels associated with the electrodes 150, and also communicate calibration information with the microcontroller 415 during calibration of the IPG 20.

The IPG 20 also includes a power supply portion 440. The power supply portion includes a rechargeable battery 445, fuse 450, power ASIC 455, recharge coil 460, rectifier 463 and data modulation circuit 465. The rechargeable battery 445 provides a power source for the power supply portion 440. The recharge coil 460 receives a wireless signal from the PPC 135. The wireless signal includes an energy that is converted and conditioned to a power signal by the rectifier 463. The power signal is provided to the rechargeable battery 445 via the power ASIC 455. The power ASIC 455 manages the power for the IPG 20. The power ASIC 455 provides one or more voltages to the other electrical and electronic circuits of the IPG 155. The data modulation circuit 465 controls the charging process.

The IPG also includes a magnetic sensor 480. The magnetic sensor 480 provides a "hard" switch upon sensing a magnet for a defined period. The signal from the magnetic sensor 480 can provide an override for the IPG 20 if a fault is occurring with the IPG 20 and is not responding to other controllers. The magnetic sensor 480 can also be used to turn on and off stimulation.

The IPG 20 is shown in FIG. 8 as having a microcontroller 415. Generally speaking, the microcontroller 415 is a controller for controlling the IPG 20. The microcontroller 415 includes a suitable programmable portion 485 (e.g., a microprocessor or a digital signal processor), a memory 490, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG 20 includes memory, which can be internal to the control device (such as memory 490), external to the control device (such as serial memory 495), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 485 executes software that is capable of being stored in the RAM (e.g., during execution), the ROM (e.g., on a generally permanent basis), or another non-transitory computer readable medium such as another memory or a disc.

Software included in the implementation of the IPG 20 is stored in the memory 490. The software includes, for example, firmware, one or more applications, program data, one or more program modules, and other executable instructions. The programmable portion 485 is configured to retrieve from memory and execute, among other things, instructions related to the control processes and methods described below for the IPG 20. For example, the programmable portion 485 is configured to execute instructions retrieved from the memory 490 for sweeping the electrodes 150 in response to a signal from the CP 22.

The PCB also includes a plurality of additional passive and active components such as resistors, capacitors, inductors, integrated circuits, and amplifiers. These components are arranged and connected to provide a plurality of electrical functions to the PCB including, among other things, filtering, signal conditioning, or voltage regulation, as is commonly known.

Pudendal and Sacral Nerve Stimulation Sweep Algorithm and Method

There are numerous concerns and issues related to electrical stimulation of the sacral nerve and/or the pudendal nerve. Many of these concerns and issues ultimately affect the functioning and efficacy of the stimulation therapy being administered. Programmed (initially programmed and reprogrammed subsequent to the initial programming) at a physician's (or other service provider's) office, meaning that a patient must travel to the office in order to have the pulse generator programmed or reprogrammed. This can be inconvenient for the patient who has to take time out of her day to go to the office, not to mention costing the patient and/or her insurance company money for the office visit. Additionally, traveling to an office to program a pulse generator can increase the amount of time that it takes to arrive at a programmed therapy that is beneficial to the patient.

To address at least these issues, the present disclosure offers systems and methods for reprogramming or automatic adjustment of the stimulation therapy without requiring a visit from the patient to a physician's (or other service provider's) office. As such, the physician need only position the stimulation leads in the correct anatomical location(s), and the IPG and/or a patient programmer will perform reprogramming of the sacral nerve stimulation therapy when loss of efficacy of the treatment is detected. For example, reprogramming is desirable if the patient is exhibiting a suboptimal clinical response to therapy. In that regard, the reprogramming involves changing stimulation parameters in order to achieve the optimal response or otherwise improve the response. The various aspects of the automatic reprogramming of the sacral nerve stimulation therapy are discussed in more detail below with reference to FIGS. 9-11. For purposes of the present disclosure, the term sacral nerve stimulation may refer to the electrical stimulation of the sacral nerve, the pudendal nerve, the sacral spinal nerve, or combinations thereof.

Figure 9:
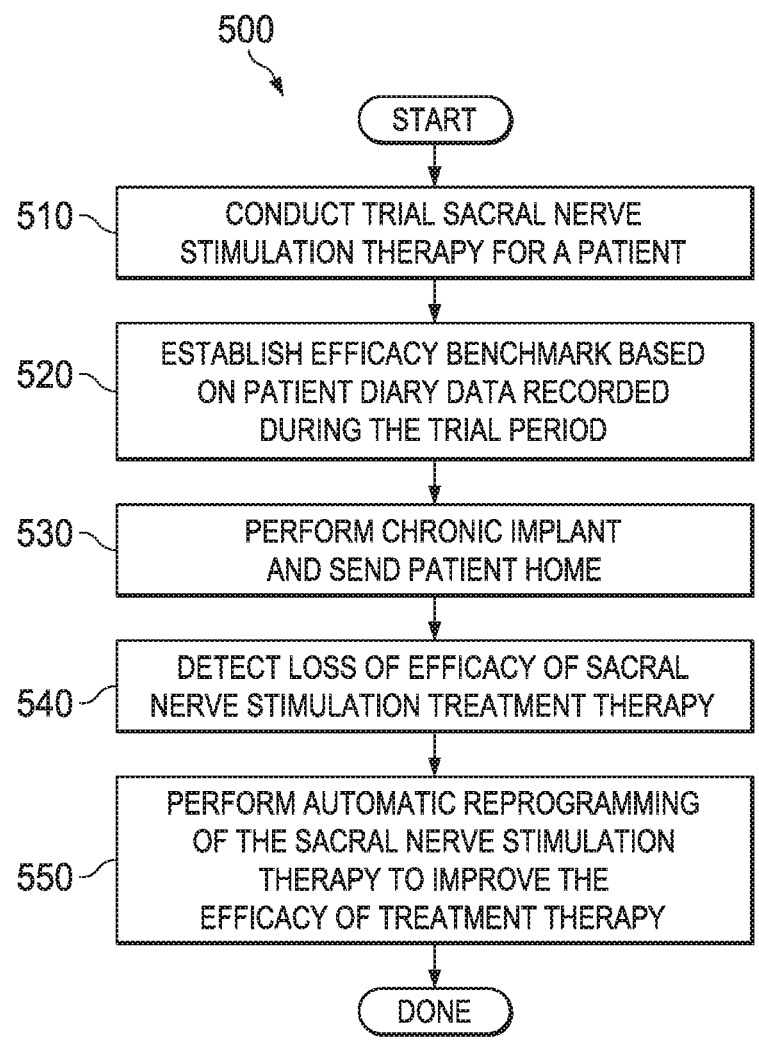
FIGS. 9-11 are flowcharts of methods for performing a stimulation therapy according to embodiments of the present disclosure.

In more detail, FIG. 9 is a simplified flowchart of a method 500 that describes a context in which the automatic reprogramming of the present disclosure takes place. The method 500 includes a step 510, in which a trial for sacral nerve stimulation therapy is conducted for a patient who would like to receive sacral nerve stimulation therapy. During the trial period, an external pulse generator (EPG) may be programmed by a clinician to generate electrical pulses according to one or more stimulation programs. The EPG is electrically coupled to a stimulation lead that has electrodes thereon. The stimulation lead is implanted inside the patient such that the electrodes can stimulate the sacral nerve or pudendal nerve via the electrical pulses generated by the EPG. The EPG is attached to or worn by the patient, who is then sent home after the programming.

The method 500 then proceeds to step 520, in which an efficacy benchmark is established based on a patient diary. In more detail, the patient is asked to record his/her voiding responses after he/she goes during the trial period. The voiding responses may include urinary incontinence, fecal incontinence, leakage episodes, pad changes, self-catheterizations, urination frequency or urges, or other types of data (such as sexual dysfunction) that can indicate an efficacy of the sacral nerve stimulation therapy. According to embodiments of the disclosure, the voiding responses are recorded by the patient via an electronic device such as the patient programmer 23 shown in FIG. 2B, which as discussed above may be implemented as either the pocket controller 104 in FIG. 3A or the patient programmer charger 106 in FIGS. 5A-5B. In other embodiments, a mobile computing device such as a smartphone or a tablet computer of the patient may also be used to perform the functions of the patient programmer 23 and therefore may also be used to record the voiding responses. Using a smartphone or a tablet computer as a patient or clinician programming device is described in more detail in U.S. patent application Ser. No. 14/245,225, filed on Apr. 14, 2014, and entitled "Systems, Devices, Components and Methods for Communicating with an IMD Using an External Communication Device and a Mobile Phone", the disclosure of which is hereby incorporated by reference in its entirety.

The recorded data pertaining to the voiding responses can be used to generate or compile an electronic patient diary. The patient diary data may be compared with the voiding response data that the patient previously collected before the trial period in order to determine how much improvement the sacral nerve stimulation therapy yields. In some embodiments, if the sacral nerve stimulation therapy yields a 50% improvement or better, the patient is considered a good candidate for sacral nerve stimulation therapy. In other embodiments, a 50% improvement is not necessary or required. For example, less than 8 voiding events per day is considered a success. Alternatively stated, other means may be employed to measure the success of the therapy, not just the percentages. Of course, the trial period may include repeated adjustment of the implanted lead and/or the tweaking of the stimulation parameters of the sacral nerve stimulation therapy based on the patient diary before the clinician deems that an optimal sacral nerve stimulation therapy (or close to optimal) is achieved. The voiding responses experienced by the patient in response to this sacral nerve stimulation therapy may be considered a benchmark of voiding responses. This benchmark may then be used later to detect loss of treatment efficacy.

The method 500 continues with step 530, in which a chronic stimulator such as the IPG 20 shown in FIGS. 2B and 7 is implanted inside the patient. The patient is then sent home and asked to continue to record the voiding responses using the electronic patient diary.

It is understood that although the electronic patient diary is described as being generated by, and stored on, the patient programmer in this example, it is not intended to be limiting. In various other embodiments, the electronic patient diary may be generated by, and stored on other devices or locations such as a smartphone or tablet computer, a laptop or desktop computer, or a remote server. In some embodiments, the electronic patient diary may be automatically uploaded to a cloud server or to a clinician programmer. The uploading may occur periodically, or immediately after the patient records new information, or it may be done in response to an explicit command from the patient or clinician.

The method 500 proceeds to step 540, in which a loss of efficacy of the sacral nerve stimulation therapy is detected. In some embodiments, the patient programmer automatically detects the loss of efficacy based on the electronic patient diary. In more detail, the patient programmer may periodically compare the current voiding responses (within the past few days or weeks) with the established benchmark. The comparison may indicate a trend such as increased incontinence or more frequent urination, which may indicate that the sacral nerve stimulation therapy has lost some of its efficacy over time. In some cases, the loss of efficacy may be due to habituation, that is, if a continuous therapy is administered, the patient can start to become acclimated to the stimulation over time, which then losses its effectiveness. In other cases, the loss of efficacy may be due to lead migration, etc.

The method 500 continues with step 550, in which automatic reprogramming of the sacral nerve stimulation therapy is performed to improve the efficacy of the therapy if the detected efficacy loss exceeds a predetermined threshold. Alternatively stated, the stimulation protocol is automatically adjusted when the loss of efficacy is deemed too excessive. In some embodiments, the reprogramming of the sacral nerve stimulation therapy involves automatically choosing, from a plurality of predefined stimulation programs, a stimulation program that best improves the treatment efficacy. Thereafter, the existing stimulation program (one that has suffered from the loss of efficacy) is replaced by the new stimulation program. This process may be referred to as a program-based sweep.

In addition to, or instead of, the program-based sweep, the reprogramming may also involve a contact-based sweep, in which a bellows-and-toes test is performed for each available electrode contact on the stimulation lead. The bellows-and-toes test will help determine which new electrode contact (if activated to replace the existing electrode contact) is most likely to improve the efficacy of the treatment. The program-based sweep and the contact-based sweep are now discussed below in more detail with reference to FIG. 10.

Figure 10A:
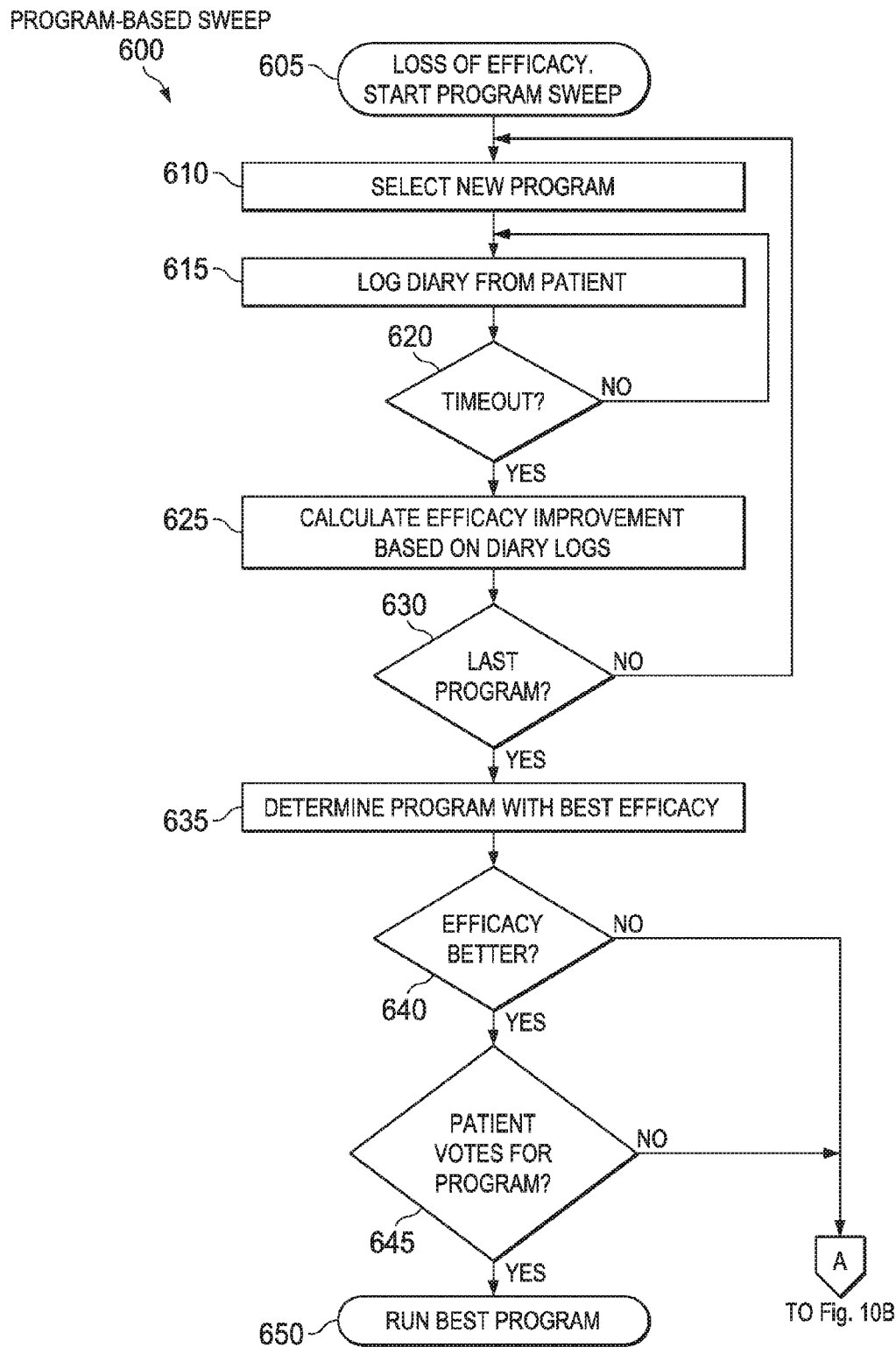
Figure 10B:
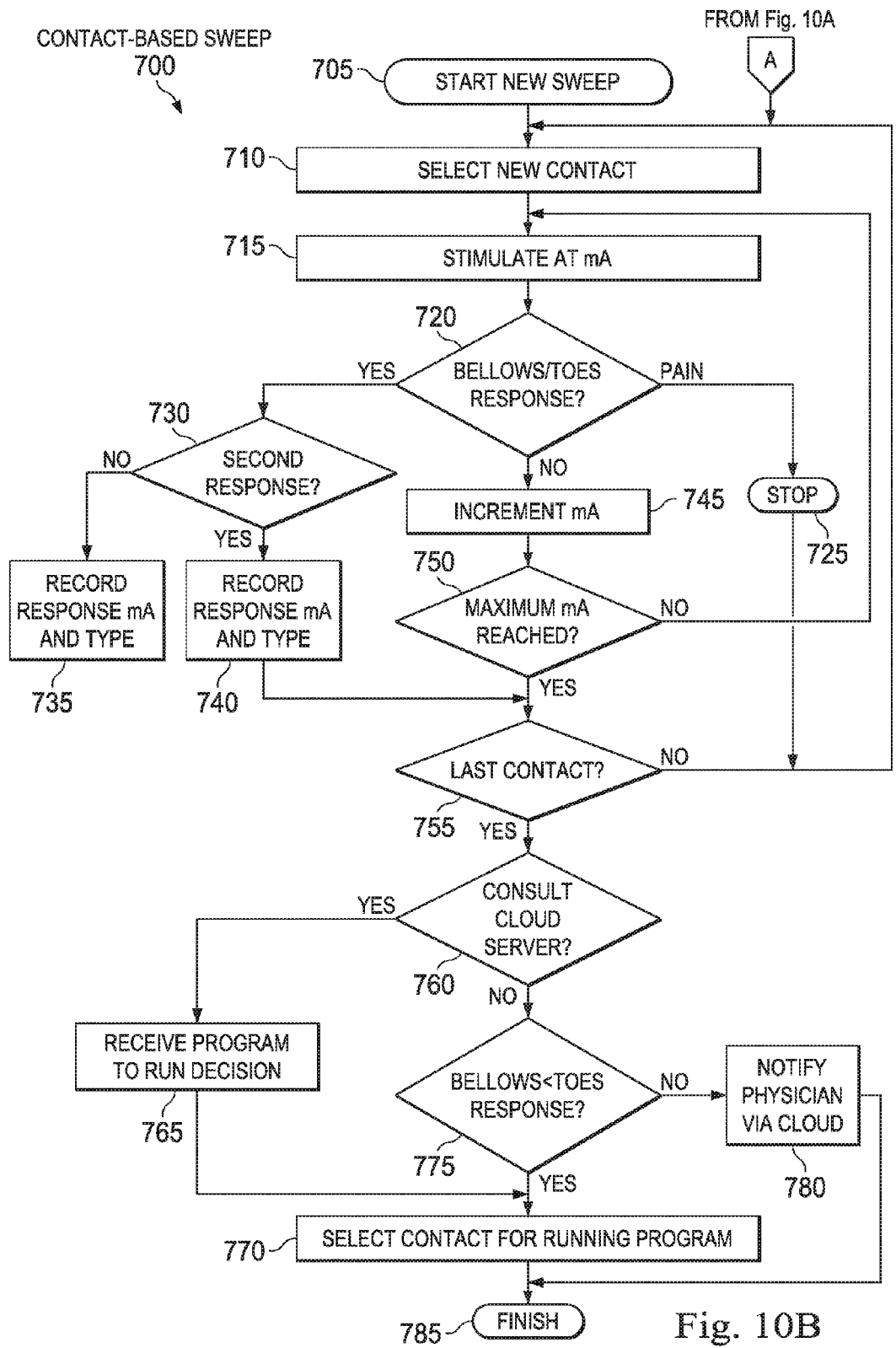

Referring to FIG. 10, a flowchart illustrates a method 600 of conducting the program-based sweep and a method 700 of conducting the contact-based sweep. The method 600 includes a step 605, in which the loss of efficacy of sacral nerve stimulation therapy is detected, and the program-based sweep is initiated. Again, the loss of efficacy may be detected by analyzing the electronic patient diary data. Alternatively, the loss of efficacy may be manually indicated by the patient. For example, the patient may subjectively "feel" that he/she is experiencing worsening incontinence symptoms and thus would like to initiate a reprogramming of the stimulation therapy. As another example, the patient may feel that the current stimulation therapy is causing discomfort such as pain, in which case the patient would also like to initiate a reprogramming of the stimulation therapy.

The method 600 continues with step 610, in which a new stimulation program is selected. In more detail, a plurality of predefined stimulation programs is stored either on the IPG, or on the patient programmer (e.g., PPC), or even on a remote server (e.g., the "cloud"). These stimulation programs have been configured by a healthcare professional at a previous patient visit to the clinic, for example during implantation of the IPG or during a post-op visit. The stimulation programs may differ from one another in terms of stimulation parameters such as electrode contact configuration (i.e., which contacts are cathodes/anodes), stimulation amplitude, stimulation frequency, or stimulation pulse width. These stimulation programs may include the current stimulation program that has now lost its efficacy and needs to be replaced. In some embodiments, the new stimulation program may be selected automatically by the patient programmer or by the IPG. In other embodiments, the patient is prompted to select the new stimulation program manually.

The method 600 continues with step 615, in which the patient programmer logs the electronic patient diary in response to the patient's input. The patient may be prompted (e.g., by the patient programmer) to keep a running log of his voiding responses after the new stimulation program has been executed. As discussed above, these voiding responses may include, but are not limited to, urinary incontinence, fecal incontinence, leakage episodes, pad changes, self-catheterizations, urination frequency or urges, or other types of data (such as sexual dysfunction) that can indicate an efficacy of the sacral nerve stimulation therapy. The patient programmer generates an updated electronic patient diary based on the voiding responses entered by the patient. The updated patient diary will provide a reliable indication of how effective the new stimulation program is in terms of treating the patient.

The method 600 continues with step 620 to decide whether or not a sufficient amount of time has passed for the new stimulation program. In more detail, the stimulation program, once turned on, may not instantly provide the optimal efficacy that the patient desires. Rather, the patient typically experiences gradual improvements in the treatment efficacy. That is, as time goes on, the stimulation program may become more and more effective, until it finally reaches its full treatment efficacy. The time period required for a particular stimulation program to reach its full efficacy may range from a few days to a few weeks. Therefore, the present disclosure may predefine an amount of time for the stimulation program to be executed before a new stimulation program is selected. In the interest of saving time, the predefined amount of time may be set to be shorter than the full amount of time that will guarantee that the fully stimulation efficacy has been reached, but long enough that it will provide a reliable indication of the efficacy of the stimulation program. For example, it may take two weeks or longer before the new stimulation program has reached its full efficacy, but since two weeks would have been too long of a period of time (especially if there are many other stimulation programs to be tried), the new program may be allowed to run two or three days, if two or three days is sufficiently long for the stimulation program to reach close to its full efficacy.

If the predetermined amount of time to run the new stimulation program has not been reached, the method 600 loops back to step 615, where the patient diary is continuously updated in response to the patient's input. If the predetermined amount of time to run the new stimulation program has been reached, the method 600 continues with step 625 to calculate the efficacy improvement based on the diary logs. In some embodiments, the efficacy of the treatment (or the improvement thereof) may be calculated as a score, which may take into account of the type of voiding responses recorded in the diary and the number of the occurrences of the voiding responses.

Once the efficacy associated with the new stimulation program has been calculated, a step 630 of the method 600 decides whether the last stimulation program has been executed. If not, a new stimulation program is executed, and the process discussed above with reference to steps 610-625 is repeated for the new stimulation program. By doing so, an efficacy evaluation may be made (e.g., in the form of an efficacy score) for each new stimulation program.

If the stimulation program that was most recently executed is the last program—meaning that all of the predefined stimulation programs stored on the patient programmer, or on the IPG, or on the cloud has been tried—the method 600 will continue with step 635 to determine which stimulation program yielded the best treatment efficacy (or the most amount of efficacy improvement over the stimulation program that needs to be replaced).

The stimulation program with the best efficacy improvement is then executed. In step 640, the patient may indicate whether the efficacy is really better. If the answer is no, then the method 700 is executed to begin the contact-based sweep. In other words, if the patient still does not think the new stimulation program (despite it being the best program out of all the available stimulation programs) is good enough, then that means a new set of electrode contacts may need to be activated to try to achieve an improvement in treatment efficacy.

Even if the patient indicates that the efficacy is better than before, the patient may still vote in step 645 on whether or not to continue with the new stimulation program. For example, in some instances, the new stimulation program may offer an improvement in efficacy, but at the same time it might cause discomfort such as pain to the patient. Therefore, the patient may decide that this is not satisfactory and may vote down the new stimulation program. In that case, the method 700 (the contact-based sweep) may be initiated. However, if the patient indicates that the efficacy is better (in step 640) and votes to go with the new stimulation program (in step 645), the method 600 may conclude in step 650, where the new (the best) stimulation program is now run to provide sacral nerve stimulation therapy for the patient.

Still referring to FIG. 10, the contact-based sweep method 700 can be initiated either by itself (i.e., standalone) in step 705, or it may be initiated based on the results of the program-based sweep method 600 discussed above. In step 710, a new electrode contact (also referred to as "electrode" or "contact") on the stimulation lead is selected. The selection of the new electrode contact may be made automatically and does not necessarily involve human input. In step 715, a stimulation current is applied to the selected contact. The initial stimulation current is set to be very low, for example 0.05 milli-amps (mA) or 0.1 mA.

Thereafter, step 720 determines where the patient is exhibiting a bellows or toes response as a result of the stimulation current being applied. A bellows response may correspond to the patient feeling a sensation in his/her bellows area, and a toes response may correspond to the patient feeling a sensation in his/her toes. In some cases, the bellows response may include a contraction in the anal region of the patient, and the toes response may include an involuntary movement of the toes of the patient.

If the patient feels pain rather than either a bellows or toes response, the method 700 proceeds to step 725 to stop stimulation, and then loops back to step 710 to select a new contact 710. This is because if the patient feels pain before the bellows or toes response, that means this particular electrode contact is unsuitable for delivering electrical stimulation, and thus a new electrode contact needs to be tried. If the patient feels no pain and actually does exhibit a bellows or toes response, the method 700 proceeds to step 730 to determine whether this is the first bellows or toes response or the second bellow or toes response. If it is not the second bellows or toes response, the response type (i.e. whether it is the bellows response, or the toes response) as well as the stimulation current amplitude are recorded. Similarly, if it is the second bellows or toes response, the response type and the stimulation current amplitude are also recorded, and the method 700 continues to step 755.

On the other hand, if the decision step 720 reveals that the patient does not feel pain but does not exhibit a bellows or toes response either, the method 700 proceeds to step 745, in which the stimulation current amplitude is increased. The absence of the bellows or toes response means that the stimulation current is not high enough yet, and thus increasing the stimulation current amplitude is necessary. To be safe, the stimulation current amplitude may be increased in small increments, such as 0.05 mA or 0.1 mA at a time. Step 750 decides whether the maximum current amplitude (may be predefined) has been reached, and if so, the method 700 proceeds to step 755. If the maximum current amplitude has not been reached, the method 700 loops back to step 715 to stimulate the same contact with an increased current amplitude and to repeat the steps 720-745.

As discussed above, for a particular electrode contact, if the second bellows or toes response is felt by the patient, or if the maximum stimulation current amplitude has been reached, the step 755 is executed to make a further decision: if this the last electrode contact? If not, then the method 700 loops back to step 710 to select a new electrode contact and to repeat the steps 715-750 again. But if the last electrode contact has been tried, then the method 700 proceeds to step 760 to decide whether a cloud server is consulted. If yes, then the cloud server is consulted, and a program to run decision is received, after which a contact for running the program is selected in step 770. If the cloud server is not consulted, the method 700 proceeds to step 775 to determine whether the bellows response occurs before the toes response. If the bellows response does not occur before the toes response, the physician is notified via the cloud in step 780. If the bellows response does occur before the toes response, the method 700 proceeds to step 780 to select the contact for running the program. The method 700 concludes at step 785.

According to the various aspects of the present disclosure, the timing of the bellows response and the toes response is important. In particular, it is desirable for the patient to exhibit a bellows response before the toes response. The reasoning is that, one of the primary goals of the sacral nerve stimulation therapy discussed herein is to treat an overactive bladder (OAB) syndrome. The overactive bladder syndrome refers to the contraction of the patient's bladder without the patient having control, even when the bladder is not full. As a result, urinary incontinence may occur. The sacral nerve stimulation therapy discussed herein treats the overactive bladder syndrome by inhibiting the unwanted contraction of the bladder. In order to do so, the sacral nerve stimulation therapy attempts to recruit nerves that exhibit motor responses, which is a bellows type response (i.e., contraction of the anal or vaginal muscles). If the bellows response occurs before the toes response, this indicates that the electrode contact (that produced the bellows response before producing the toes response) is close to the target location of the nerve that would treat the overactive bladder. But if a toes response occurs before the bellows response, that indicates the electrode contact is still somewhat far away from the target nerve location, which means the electrode contact is not optimal for treating the overactive bladder.

Therefore, the contact-based sweep discussed above steps through each electrode contact on the stimulation lead and determines whether each given electrode contact is a suitable electrode contact (and offers an improvement over the previous electrode contact) for delivering electrical pulses of the sacral nerve stimulation therapy. Specifically, if a bellows response occurs before a toes response, the electrode contact is deemed good, but if a toes response occurs before a bellows response, that electrode contact is deemed not good. If the bellows response before the toes response occurs for two or more electrode contacts, then the electrode contact that generates the bellows response at a lower stimulation current may be considered better than the electrode contact that generates the bellows response at a higher stimulation current.

Also as illustrated by the steps of the method 700 in FIG. 10, the bellows and toes response test involves ramping up a stimulation amplitude. It is also understood that the same test may be run by ramping up other stimulation parameters such as stimulation frequency and stimulation pulse width, rather than the stimulation amplitude. In some embodiments, the ramping up of the stimulation amplitude, frequency, and pulse width may be performed as a nested loop, which for reasons of simplicity is not specifically illustrated herein, but its execution is relatively straightforward and is understood by a person of ordinary skill in the art. At the end of the ramping up process (whether it's for only one of the stimulation parameters, or if it's for the nested loop), one or more electrode contacts may be identified as being optimal electrode contacts for the sacral nerve stimulation therapy discussed herein. The particular values (e.g., amount of stimulation amplitude, frequency, or pulse width) for the stimulation parameters that correspond with the occurrence of the bellows response may be considered thresholds or starting values for these stimulation parameters.

Thereafter, a stimulation program may be created specifically for each of these "good" electrode contacts based on the identified values of the stimulation parameters. It is also understood that the electrode contacts may have different values for the stimulation parameters when the bellows response (before the toes response) occurs. For example, electrode contact 1 may have a bellows response at a stimulation amplitude of 2.1 mA, a stimulation frequency of 20 pulse/second, and a pulse width of 200 microseconds, whereas electrode contact 2 may have a bellows response at a stimulation amplitude of 2.5 mA, a stimulation frequency of 15 pulse/second, and a pulse width of 200 microseconds. In other words, the contact-based sweep discussed above not only identifies the best electrode contacts for applying sacral nerve stimulation therapy, but it also helps determine the values of the stimulation parameters to use for the stimulation program to be delivered by each electrode contact.

Based on the discussions above, it can be seen that the present disclosure offers systems, devices, and methods of detecting loss of treatment efficacy, and based on the detected efficacy, automatically adjusting the stimulation therapy to improve the efficacy. In some embodiments, the loss of treatment efficacy may be detected based on an analysis of the electronic patient diary. In other embodiments, the patient may indicate a loss of treatment efficacy by manually engaging the patient programmer (e.g., clicking on a physical or virtual button on the programmer), or by emailing or calling the clinician to inform him as such. In response to the detected loss of efficacy, the automatic stimulation therapy adjustment may include a program-based sweep to determine which one of a plurality of predefined stimulation programs should be used. In addition, the automatic stimulation therapy adjustment may also include a contact-based sweep, which involves detecting a bellows and toes response from the patient, and based on the timing of the bellows and toes responses, determining which electrode contact to use and the stimulation parameter values for that electrode contact.

The setting for the automatic stimulation therapy adjustment/reprogramming may be at the patient's home, and the entire process discussed above may be applied without the clinician's involvement. After the reprogramming is complete, the patient programmer may automatically send a message to the clinician to inform him/her that the sacral nerve stimulation therapy has been automatically reprogrammed or adjusted for the patient. In other embodiments, the clinician may be involved in the reprogramming process. For example, after the loss of efficacy is detected, the clinician is informed (e.g., by the patient programmer sending the clinician a message), and the patient may still need a confirmation code from the clinician to initiate the automatic reprogramming process.

Alternatively, the program-based sweep and the contact-based sweep discussed above may not necessarily be done in response to a detected loss of treatment efficacy, but are rather performed to establish initial efficacy for a new patient. In other words, the sweeps may be done to help the clinician determine the best electrode contacts to apply the stimulation, and the specific stimulation parameter values to use for the stimulation programs. Thus, in some embodiments the sweeps may take place at a clinic during the actual implantation of the lead or the implantation of the IPG. The sweeps may also be performed during the patient's post-op visit. In these scenarios, the sweeps may also be performed via clinician programmer, or a smartphone or tablet computer at the clinic.

Figure 11:
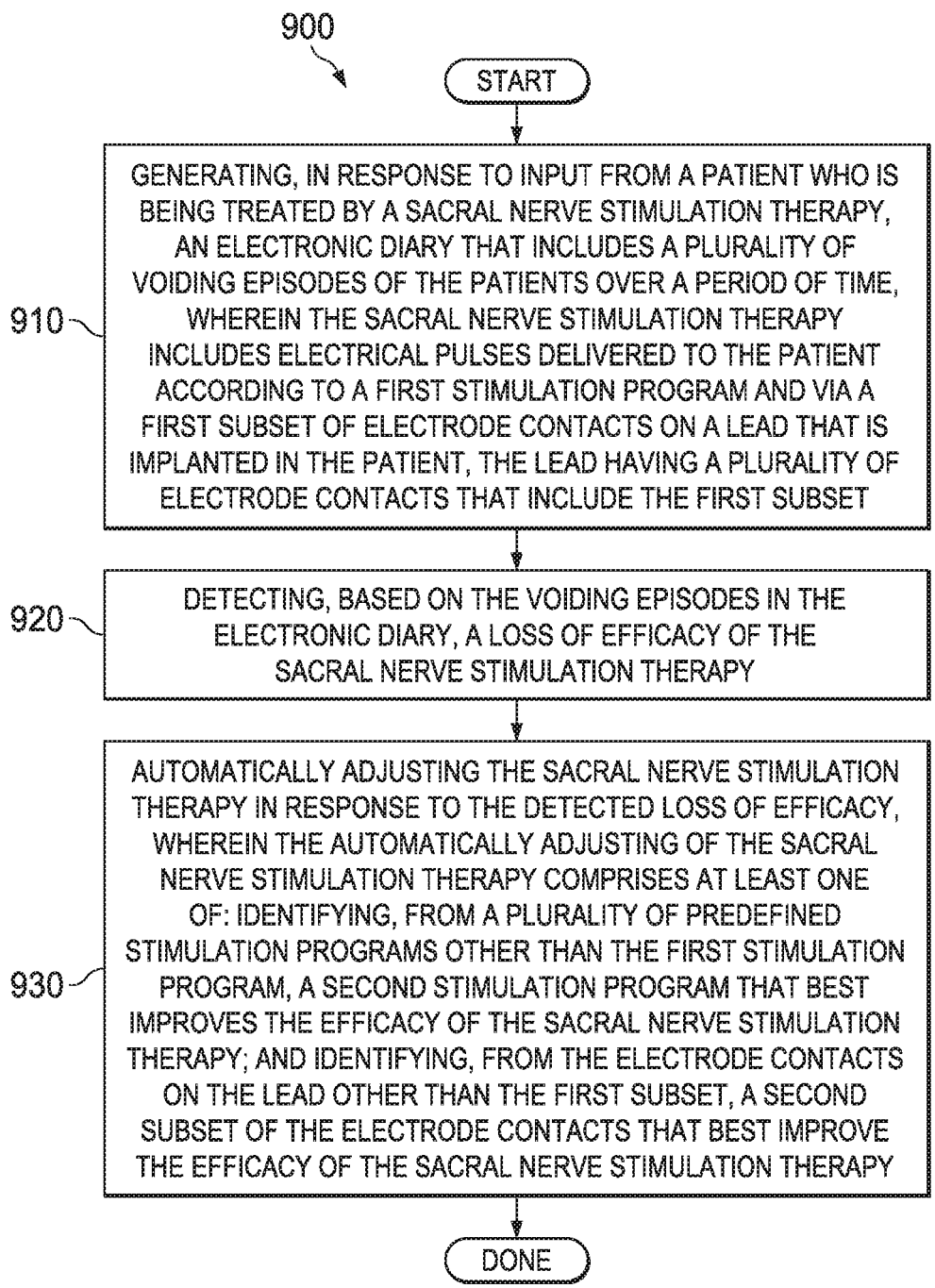

FIG. 11 is a flowchart illustrating a simplified method 900 of automatically adjusting a stimulation therapy to improve efficacy of the stimulation therapy according to an embodiment of the present disclosure. The method 900 includes a step 910 of generating, in response to input from a patient who is being treated by a sacral nerve stimulation therapy, an electronic diary that includes a plurality of voiding responses of the patient over a period of time. The sacral nerve stimulation therapy includes electrical pulses delivered to the patient according to a first stimulation program and via a first subset of electrode contacts on a lead that is implanted in the patient. The lead has a plurality of electrode contacts that include the first subset.

The method 900 includes a step 920 of detecting, based on the voiding responses in the electronic diary, a loss of efficacy of the sacral nerve stimulation therapy.

The method 900 includes a step 930 of automatically adjusting the sacral nerve stimulation therapy in response to the detected loss of efficacy. In some embodiments, the automatic adjusting of the sacral nerve stimulation therapy comprises identifying, from a plurality of predefined stimulation programs other than the first stimulation program, a second stimulation program that best improves the efficacy of the sacral nerve stimulation therapy. In some embodiments, the automatic adjusting of the sacral nerve stimulation therapy comprises identifying, from the electrode contacts on the lead other than the first subset, a second subset of the electrode contacts that best improve the efficacy of the sacral nerve stimulation therapy.

In some embodiments, the identifying of the second stimulation program further comprises the following steps: applying one of the predefined stimulation programs other than the first stimulation program; thereafter prompting the patient to record voiding responses in the electronic diary over a specified period of time; determining, based on the recorded voiding responses in response to the applied one of the predefined stimulation programs, a degree of improvement of the efficacy of the sacral nerve stimulation therapy; repeating the applying, the prompting, and the determining a plurality of times, wherein a different one of the predefined stimulation program is applied each time; and selecting the predefined stimulation program that yielded the most efficacy improvement as the second stimulation program.

In some embodiments, the identifying the second subset of the electrode contacts further comprises: ramping up a stimulation parameter for one of the electrode contacts other than the first subset of the electrode contacts; determining, as the stimulation parameter is being ramped up, whether the patient experiences a bellows response before a toes response; selecting said electrode contact as a member of the second subset of the electrode contacts in response to the patient experiencing the bellows response before the toes response; and repeating the ramping up and the determining a plurality of times, wherein a different one of the electrode contacts is used each time. In some embodiments, the stimulation parameter being ramped up includes stimulation current amplitude, pulse width, or frequency. In some embodiments, the method further comprises: configuring a stimulation program to be applied through the second subset of the electrode contacts. The configuring of the stimulation program comprises setting a starting value of the stimulation parameter as a function of a value of the stimulation parameter that yielded the bellows response.

In some embodiments, one or more of the generating of the electronic diary, the detecting of the loss of efficacy, and the automatic adjusting of the sacral nerve stimulation is performed using a portable handheld electronic device of the patient. In some embodiments, the portable handheld electronic device includes one of: a patient programmer, a smartphone, or a tablet computer.

In some embodiments, the generating of the electronic diary, the detecting of the loss of efficacy, and the automatic adjusting of the sacral nerve stimulation are performed at a non-clinical setting and without direct involvement of a medical professional.

It is understood that the method 900 may include additional steps that may be performed before, during, or after the steps 910-930 discussed above. For example, the method

900 may include a step of applying the second stimulation program to the patient. As another example, the method 900 may further include cycling or changing the laterality of the stimulation of the nerve to avoid habituation. As discussed above, habituation refers to the situation that if a continuous therapy is administered, the patient can start to become acclimated to the therapy over time, and the therapy can lose its effectiveness. In some instances, continuous electrical stimulation over prolonged periods of time can also result in damage to the pudendal and/or sacral nerves. Therefore, cycling or and/or changing the laterality of the stimulation of the nerve may be applied to guard against habituation and/or nerve damage.

For example, the IPG may be programmed to stimulate the nerve for a period of time and then cease or otherwise alter stimulation momentarily in order to give the nerve a break. In some embodiments, the IPG is configured to change the laterality of the stimulation by cycling between stimulation of the right side of the nerve for a period of time (e.g., 30 seconds) and stimulation of the left side of the nerve for a period of time (e.g., 30 seconds). In some further embodiments, the IPG is configured to cycle through bilateral nerve stimulation in addition to stimulating the right and left sides of the nerve or instead of stimulating one of the left and right sides of the nerve. If habituation is identified with respect to a patient, the IPG can go through a number of cycles to see which one (or combination) is right for the patient, since it is not generally known what the optimal cycling pattern is for the particular patient. In some examples, the patient can pick the one or more stimulations of the cycle that are comfortable or otherwise desired, for instance, by using a user input device such as the patient programmer or via a patient feedback tool (PFT) discussed in more detail in U.S. Patent Application No. 2012/0310305, filed on May 31, 2011, and entitled "Patient handheld device for use with a spinal cord stimulation system" to Kaula, et al., the disclosure of which is hereby incorporated by reference in its entirety. In some embodiments, the patient can choose right and/or left side stimulation, stimulation location (electrode location and/or number), or the like, via the patient programmer or the PFT. For reasons of simplicity, other additional steps are not discussed in detail herein.

The present devices, systems, and methods described herein include various benefits/advantages. It is understood, however, that not all benefits/advantages are necessarily discussed herein, different embodiments may offer different advantages, and no particular advantage is required for all embodiments. For instance, the present devices, systems, and methods can save the patient trips to the physician, thereby decreasing cost of care because trips to the physician's office to reprogram are expensive billable events. Moreover, the present devices, systems, and methods increase the attractiveness of the therapy because the reprogramming occurs more quickly and at a reduced cost from previous systems.

The quicker reprogramming allows the therapy to remain effective or become effective again, rather than having the patient wait for scheduling of an appointment to reprogram the stimulation device, thereby keeping the patient in an optimal range more of the time. The present devices, systems, and methods described herein also include various benefits to a company supporting the stimulation devices and systems. Companies usually maintain numerous individuals tasked with reprogramming devices. The present devices, systems, and methods take the burden off the company for reprogramming, thereby negating the need to keep such a large number of people on board to reprogram devices.

In some examples, the present devices, systems, and methods allow the physician or other individual to get feedback from a patient base, including, but not limited to, how many people are using the stimulation device, the number of events experienced, how often devices are being reprogrammed, when was the last reprogram of each of the patients, etc. In some examples, reprogramming can be done using predefined programs, by programs selected on the basis of key events, and/or by cloud-based computing (using database and algorithm at central server and data from a patient base) to compute the best set of programming parameters for the patient. In this way, information from a patient population can be used to arrive at the best parameters for a given patient.

Another aspect of the present disclosure involves using patient's physiological response to stimulation to determine how well a stimulation lead is implanted. For pudendal nerve stimulation, there are no boney landmarks of the patient available to help guide the placement of a stimulation lead. In addition, the pudendal nerve is a sensory nerve and may not be able to produce any motor responses to help guide the placement of the stimulation lead. As such, the placement of a pudendal nerve stimulation lead has traditionally been difficult and could benefit from automated or computerized guidance. In comparison, for sacral lead placement, the physician has boney landmarks of the patient and should generally know how the nerve travels with respect to the landmarks. Also, with sacral lead placement, there are sensory and visible motor responses (such as bellows or toes responses, heel rotation, anal clamping, etc.). Due to these factors, the placement of a lead for sacral nerve stimulation is easier than for pudendal nerve stimulation. Nevertheless, the placement of a sacral nerve stimulation lead may still benefit from automated or computerized guidance so as to improve the targeting of the desired nerve location.

The present disclosure offers a system and method that uses an anal electrode device to measure a patient's physiological response to stimulation in order to determine the lead placement accuracy. In some embodiments, the patient's physiological response includes a compound motor action potential (CMAP). The various aspects of the system and method are discussed below in detail with reference to FIGS. 12-16.

Figure 12:
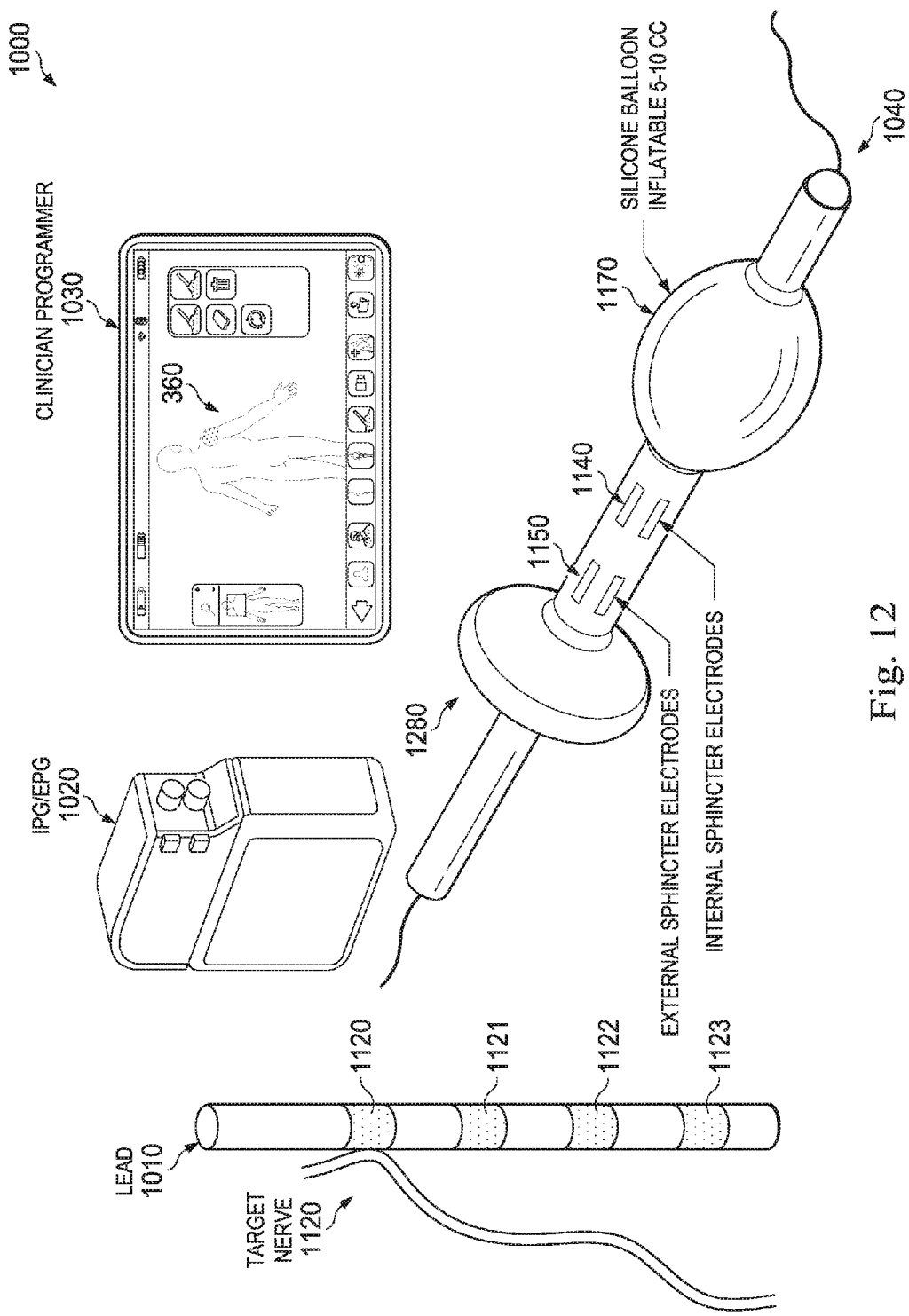
FIG. 12 illustrates an example embodiment of a system that measures a patient's physiological feedback in response to stimulation according to embodiments of the present disclosure.

FIG. 12 illustrates an example embodiment of such system 1000 that measures the patient's CMAP in response to stimulation. In more detail, the system 1000 includes a stimulation lead 1010, a pulse generator 1020, an electronic programmer 1030, and an anal electrode device 1040. The stimulation lead 1010 may be implemented as an embodiment of the lead 10 of FIG. 2B. The stimulation lead 1010 has a plurality of electrode contacts, for example electrodes 1100-1103, each of which is capable of delivering an electrical pulse to a target nerve 1120. In some embodiments, the target nerve 1120 is a pudendal nerve. In some other embodiments, the target nerve 1120 is a sacral nerve. In yet other embodiments, the target nerve 1120 is a sacral spine nerve. In the context of the present disclosure, the stimulation lead 1010 is implanted inside the pelvic region of the patient to stimulate the target nerve 1120.

The pulse generator 1020 is electrically coupled to the stimulation lead 1010. In some embodiments, the pulse generator 1020 is an external pulse generator (EPG) that can be worn by the patient in a trial phase. In some other embodiments, the pulse generator 1020 is an IPG, for example the IPG 20 shown in FIGS. 2B and 7. Regardless of whether the pulse generator 1020 is implemented as an IPG or an EPG, it generates the electrical pulses for the sacral nerve stimulation therapy that are then delivered to the target nerve 1120 through the electrode contacts 1120-1123 on the lead 1010.

The pulse generator 1020 is also electrically coupled to the electronic programmer 1030. In some embodiments, the electronic programmer 1030 may be the clinician programmer 22 shown in FIGS. 2B and 8. In other embodiments, the electronic programmer 1030 may be a smartphone or a tablet computer that are specifically configured to function as a clinician programmer, which is described in more detail in U.S. patent application Ser. No. 14/245,225, filed on Apr. 14, 2014, and entitled "Systems, Devices, Components and Methods for Communicating with an IMD Using an External Communication Device and a Mobile Phone", the disclosure of which is hereby incorporated by reference in its entirety. The electronic programmer 1030 configures the pulse generator 1020 so that it can deliver a suitable electrical stimulation therapy to the patient.

The anal electrode device 1040 is partially inserted into the patient's rectum or anus. In more detail, the anal electrode device 1040 has a plurality of internal sphincter electrodes 1140 and a plurality of external sphincter electrodes 1150. The internal and external sphincter electrodes 1140 and 1150 are sensory electrodes that are configured to sense or detect the patient's physiological response to electrical. In the present embodiment, the patient's physiological response to stimulation is manifested as electrical signals such as compound motor action potential (CMAP). When the anal electrode device 1040 is correctly inserted into the anal canal, the internal sphincter electrodes 1140 come into contact with an internal anal sphincter of the patient, and the external sphincter electrodes 1150 come into contact with an external anal sphincter of the patient. The anal electrode device 1170 also includes an inflatable balloon 1170 to prevent the anal electrode device 1040 from slipping out of the anal canal once the anal electrode device 1170 has been inserted.

The anal electrode device 1040 is also electrically and telecommunicatively coupled to the electronic programmer 1030. When electrical stimulation pulses are delivered to the target nerve 1120 through the electrode contacts 1120-1123 on the lead 1010, the sensory internal and external sphincter electrodes 1140 and 1150 pick up the CMAP signals generated by the patient in response to the electrical stimulation. The CMAP signals are then sent back to the electronic programmer 1030 for analysis. The analysis of the CMAP signal will indicate how well the stimulation lead 1010 is implanted.

Figure 13A:
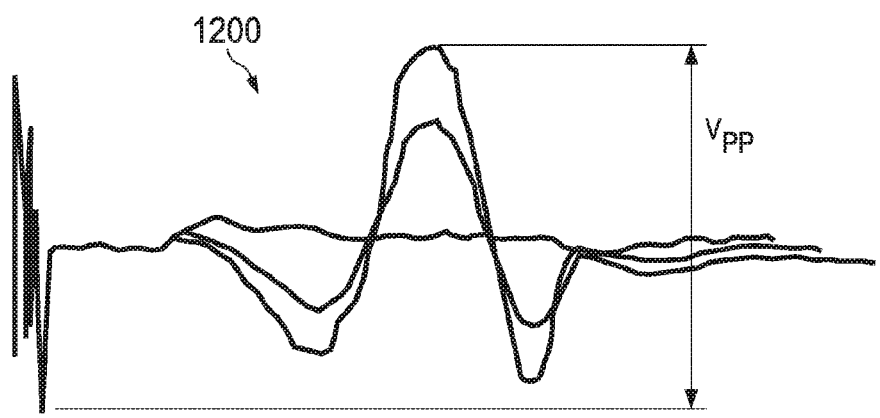
FIG. 13A illustrates example physiological signals from a patient in response to electrical stimulation according to various aspects of the present disclosure.
Figure 13B:
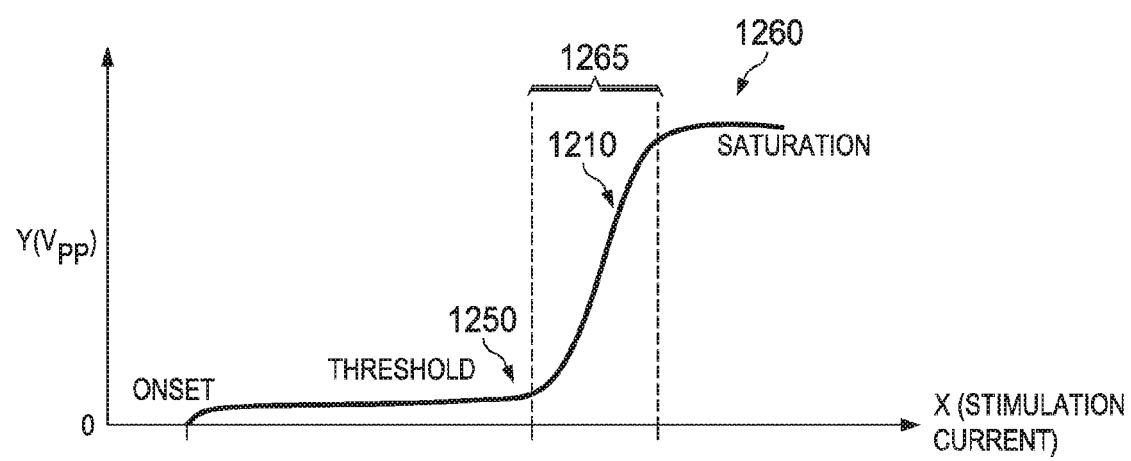
FIG. 13B illustrates an example recruitment curve plot according to various aspects of the present disclosure.

In more detail, referring now to FIGS. 13A and 13B, where FIG. 13A illustrates various example CMAP signals 1200 (measured as a peak-to-peak voltage Vpp), and FIG. 13B illustrates a plot 1210 of CMAP (Vpp) versus stimulation current. The CMAP signals 1200 shown in FIG. 13A are graphed over time (i.e., X-axis being time) and are collected from the sensory electrodes of the anal electrode device 1040 discussed above with reference to FIG. 12. It is understood that a separate CMAP signal may be collected from each sensory electrode and in response to each different stimulation pulse.

For each given sensory electrode, the amplitude of the stimulation current (delivered by the lead 1010 to the target nerve 1120) may be steadily ramped up while the CMAP produced in response thereto is measured from the anal electrode device 1040. The corresponding plot of the CMAP signals (Vpp) generated in response to the ramping up of the stimulation current is the plot 1210 shown in FIG. 13B, which may also be referred to as a recruitment curve.

As FIG. 13B illustrates, the CMAP signal is initially very low when the stimulation current amplitude is low. As the stimulation current amplitude is ramped up, the CMAP signal remains low for a period of time, until at a threshold 1250 (i.e., the "knee" of the plot/curve 1210) where the CMAP signal suddenly "jumps up." As the stimulation current amplitude continues to ramp up beyond the threshold 1250, the CMAP signal increases rapidly for a while. Eventually, saturation 1260 is reached, and the CMAP signal plateaus even though the stimulation current amplitude continues to be ramped up.

Therefore, the plot 1210 shows that if the stimulation amplitude is too low (below the threshold 1250), the stimulation therapy does not work, since the low CMAP signal indicates that the target nerves are not being recruited. On the other hand, if the stimulation amplitude is too high (in saturation 1260), such high stimulation current unnecessary because it does not produce a correspondingly greater CMAP signal. Furthermore, the excessive stimulation current may actually end up hurting the patient. As such, the stimulation "sweet spot" is somewhere beyond the threshold 1250 but before the saturation 1260 is reached. For example, the sweet spot may be somewhere in a zone/region 1265 as shown in FIG. 13B.

In addition, the plot 1210 is affected by the proximity of the stimulation electrode contacts 1120-1123 (and thus the placement of the lead 1010) to the target nerve 1120. Generally, the closer a particular electrode contact 1120-1123 (whichever contact is being tested) is to the target location of the pudendal nerve or sacral nerve to be stimulated, the "sooner" the threshold 1250 is reached. Stated differently, as the stimulation lead 1010 gets placed closer to the ideal implant location (i.e., when its electrode contacts 1120-1123 are at the optimal location for stimulating the target nerve 1120), the plot 1210 will "shift to the left" on the X-axis. In other words, a lower stimulation current amplitude is needed to reach the stimulation threshold 1250 as the stimulation lead 1010 gets positioned closer to its ideal implant location.

Accordingly, the stimulation lead 1010 may be moved, shifted, and otherwise repositioned inside the patient's body as the plot 1210 is updated (i.e., a CMAP versus stimulation current amplitude sweep is conducted for each implant location). The behavior and shape of the plot 1210 will indicate how well the stimulation lead 1010 is implanted. In some embodiments, the implant location that corresponds to the lowest threshold 1250 is selected as the target implant location for the lead 1010. In addition, the stimulation current amplitude corresponding to the threshold 1250 may also be selected as a starting value for the stimulation current amplitude for creating a stimulation program to be delivered by that corresponding electrode contact.

Since there a plurality of electrode contact 1120-1123 on the stimulation lead 1010, a "middle electrode" (i.e., the electrode 1121 or 1122 in this case) is selected to perform the CMAP VS stimulation current amplitude sweep discussed above in order to determine the optimal lead placement location. In this manner, if the lead 1010 migrates after implantation, electrodes 1120 or 1123 may still be used to provide stimulation.

It is understood that the plot 1210 (or a similar one thereof) may also be generated as a sweep of CMAP versus stimulation pulse width. In some embodiments, the generation of the plot 1210 may be performed as a nested loop of CMAP versus stimulation current amplitude and pulse width, which for reasons of simplicity is not specifically illustrated herein, but its execution is relatively straightforward and is understood by a person of ordinary skill in the art. In that case, the threshold would correspond to the lowest combination of stimulation current amplitude and pulse width.

Figure 14C:
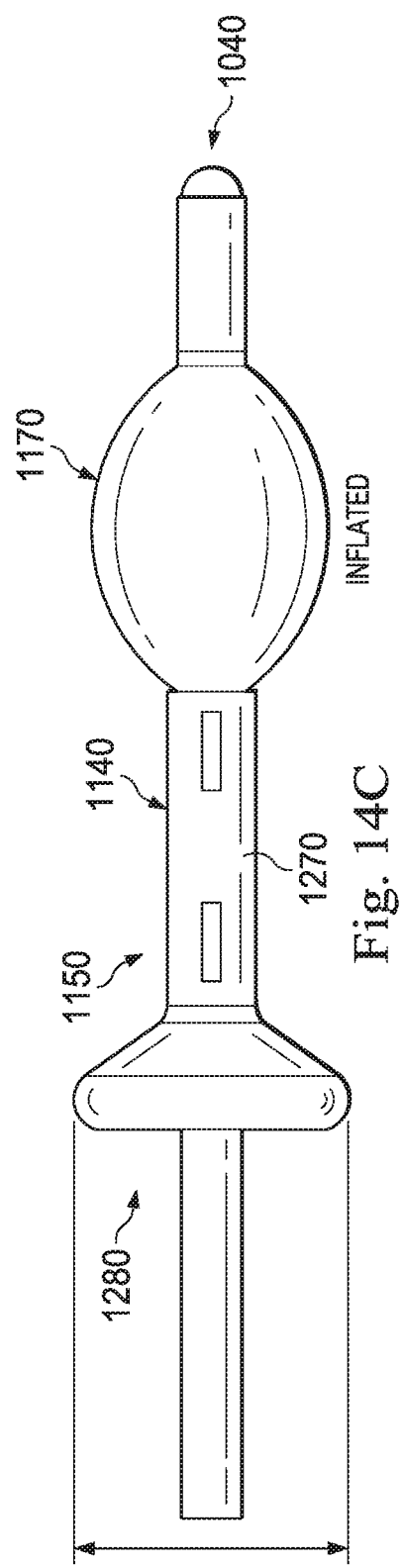

The anal electrode device 1040 is now discussed in more detail with reference to FIGS. 14A-C. Specifically, FIG. 14A is a diagrammatic perspective view of the anal electrode device 1040, FIG. 14B is a diagrammatic cross-sectional view of the anal electrode device 1040 with the balloon 1170 in a deflated state, and FIG. 14B is a diagrammatic cross-sectional view of the anal electrode device 1040 with the balloon 1170 in an inflated state. The balloon 1170 is located on an inside portion of the anal electrode device 1040 to aid in holding the anal electrode device 1040 within the anal canal. In some examples, the anal electrode device 1040 can be inserted within the anal canal of the patient while the balloon 1170 is deflated. After the insertion of the anal electrode device 1040, the balloon 1170 can then be partially or wholly inflated to hold the anal electrode device 1040 in place within the anal canal and guard against the anal electrode device 1040 from being inadvertently pulled or otherwise falling out of the anal canal.

In the embodiment shown in FIGS. 14A-14C, the anal electrode device 1040 includes an elongate and cylindrically-shaped shaft/body 1270. The internal sphincter electrodes 1140 are located on a first region of the shaft 1270, while the external sphincter electrodes 1150 are located on a second region of the shaft 1270. Once the anal electrode device 1040 is correctly inserted into the anal canal of the patient, the first region of the shaft 1270 corresponds with the internal anal sphincter of the patient, and the second region of the shaft 1270 corresponds with the external anal sphincter of the patient. In other words, the internal sphincter electrodes 1140 are configured to come into physical contact with (or at least come in close proximity with) the internal anal sphincter of the patient, while the external sphincter electrodes 1150 are configured to come into physical contact with (or at least come in close proximity with) the external anal sphincter of the patient.

In the illustrated embodiment, the internal sphincter electrodes 1140 are implemented as a ring of rectangular-shaped electrodes around the shaft 1270, as are the external sphincter electrodes 1150. Each ring of electrodes includes four separate electrodes, though it is understood that alternative embodiments may implement the internal sphincter and external sphincter electrodes 1140 and 1150 differently, for example with more or less than two rings of electrodes, and/or more or less than 4 electrodes per ring, and/or the electrodes may be shaped differently than a rectangle. In some examples, the electrodes 1140/1150 are rotatable with respect to an end of the anal electrode device 1040 to allow for rotation of the electrodes 1140/1150 to better position themselves with respect to the internal and external sphincters of the patient. In the present embodiment, to rotate the electrodes 1140/1150, the shaft 1270 is also rotated. In some embodiments, the electrodes 1140/1150 are also longitudinally slidable with respect to the end of the anal electrode device 1040 to allow for longitudinal repositioning of the electrodes 1140/1150 with respect to the internal and external sphincters of the patient. In other words, the spacing of the front and back electrodes 1140/1150 can be adjusted according to the patient subject.

The implementation of the two separate rings of electrodes 1140 and 1150 allows for four distinctive CMAPs: internal sphincter left CMAP, internal sphincter right CMAP, external sphincter left CMAP, and external sphincter right CMAP. As discussed above, the CMAP versus stimulation current amplitude or pulse width sweep can be performed with respect to each of the four distinct CMAPs.

As shown in FIGS. 14A-14C, the anal electrode device may also include an oblong (for instance, ovular) end 1280 to aid in holding the anal electrode device 1040 in place with respect to the buttocks of the patient. That is, the shape of the end 1280 of the anal electrode device 1040 is configured to fit between the left and right buttocks of the patient and inhibit rotation of the anal electrode device 1040. For instance, with an oblong shape, the end 1280 would fit between the left and right buttocks better in one direction (with the longer dimension in line with the gluteal cleft) than in another direction (with the longer dimension not in line with the gluteal cleft), thereby holding the anal electrode device 1040 in a particular orientation with respect to the patient.

In some embodiments, the anal electrode device 1040 can be custom designed to conform to the anatomy of the patient. That is, rather than just being cylindrically shaped, the anal electrode device 1040 can include a shape conforming to the anal canal of the patient. In that regard, images of the patient's anatomy can be taken and used to custom produce the anal electrode device 1040 using, for instance, three-dimensional printing or other manufacturing techniques.

Figure 15:
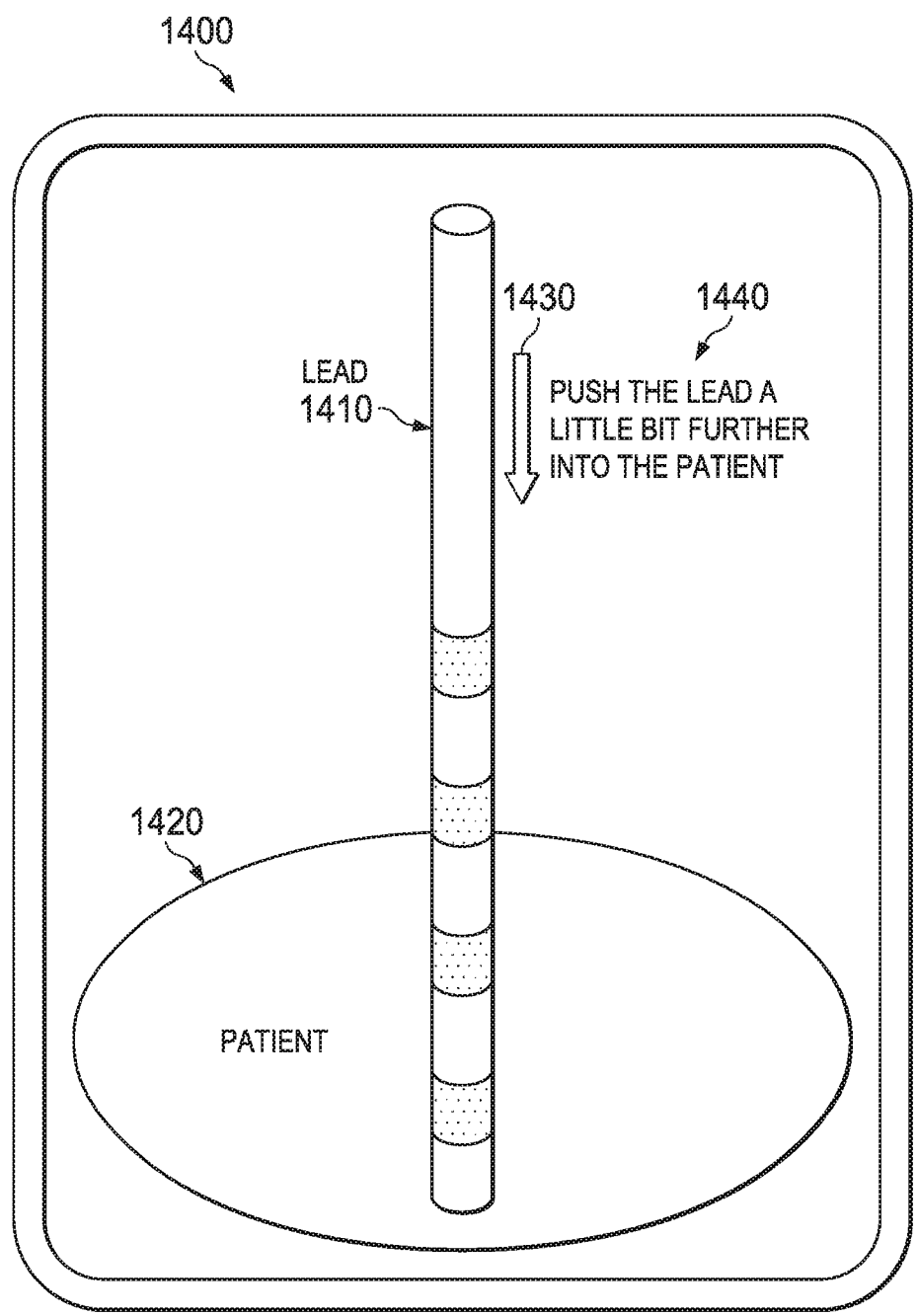
FIG. 15 is an illustration of a graphical user interface of an electronic programmer according to embodiments of the present disclosure.

FIG. 15 is a portion of a graphical user interface 1400 of the electronic programmer 1030 according to various aspects of the present disclosure. The graphical user interface 1400 illustrates visual and/or textual instructions for the clinician on how to reposition the stimulation lead 1010 based on the CMAP sweeps discussed above. For example, the graphical user interface 1400 displays a virtual representation of a lead 1410 positioned with respect to a virtual representation of a patient 1420. The user interface 1400 also displays visual instructions such as an arrow 1430 to show how the lead 1410 should be moved in or out with respect to the patient 1420, in order to arrive at its target implant location. Furthermore, textual instructions 1440 may also be displayed along with, or instead of, the visual instructions such as the arrow 1430.

Figure 16:
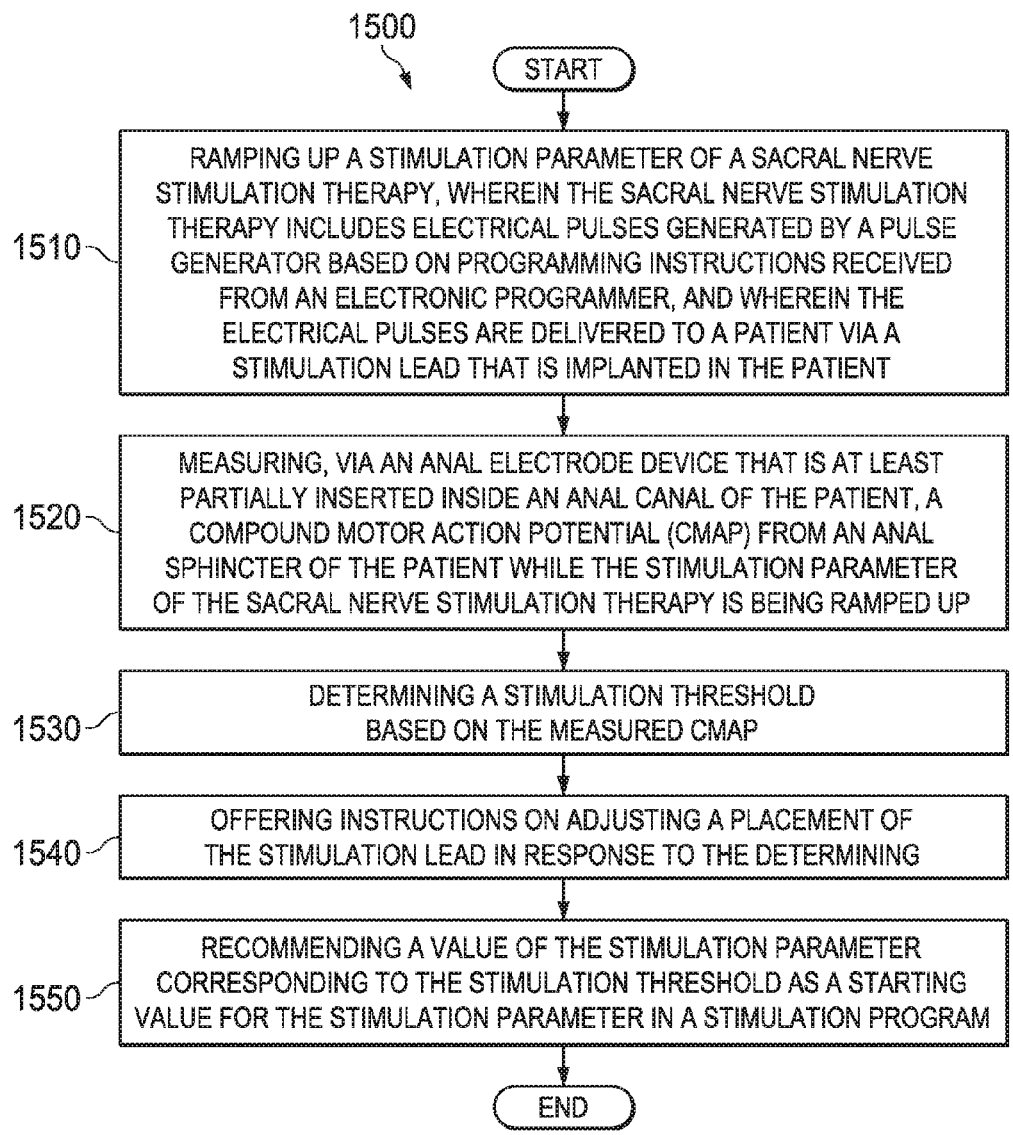
FIG. 16 is a flowchart of a method of measuring a patient's physiological feedback in response to electrical stimulation according to embodiments of the present disclosure.

FIG. 16 is a simplified flowchart of a method 1500 of measuring a physiological feedback from a patient in response to electrical stimulation according to various aspects of the present disclosure. The method 1500 includes a step 1510 of ramping up a stimulation parameter of a sacral nerve stimulation therapy. The sacral nerve stimulation therapy includes electrical pulses generated by a pulse generator based on programming instructions received from an electronic programmer. The electrical pulses are delivered to a patient via a stimulation lead that is implanted in the patient. In some embodiments, the stimulation parameter being ramped up includes a stimulation amplitude or a stimulation pulse width. In some embodiments, the stimulation lead includes a plurality of electrode contacts.

The method 1500 includes a step 1520 of measuring, via an anal electrode device that is at least partially inserted inside an anal canal of the patient, a compound motor action potential (CMAP) from an anal sphincter of the patient while the stimulation parameter of the sacral nerve stimulation therapy is being ramped up. In some embodiments, the anal electrode device includes: a first ring of sensory electrodes corresponding to an internal sphincter of the patient; and a second ring of sensory electrodes corresponding to an external sphincter of the patient. In some embodiments, the anal electrode device includes an inflatable balloon. In some embodiments, the step 1520 of measuring comprises obtaining the CMAP from at least one of the sensory electrodes of the first ring or the second ring.

The method 1500 includes a step 1530 of determining a stimulation threshold based on the measured CMAP.

The method 1500 includes a step 1540 of offering instructions on adjusting a placement of the stimulation lead in response to the determining. In some embodiments, the step 1540 of offering comprises displaying graphical or textual instructions via a graphical user interface of the electronic programmer.

The method 1500 includes a step 1550 of recommending a value of the stimulation parameter corresponding to the stimulation threshold as a starting value for the stimulation parameter in a stimulation program.

It is understood that the method 1500 may include additional steps that may be performed before, during, or after the steps 1510-1530 discussed above. For example, the method 1500 may include a step of repeating the ramping up, the measuring, and the determining for each of the electrode contacts on the stimulation lead. For reasons of simplicity, other additional steps are not discussed herein in detail.

The present devices, systems, and methods described herein include various advantages. It is understood, however, that not all advantages are necessarily discussed herein, different embodiments may offer different advantages, and no particular advantage is required for all embodiments. One advantage involves the use of the anal electrode device 1040 to measure the patient's physiological response (e.g. CMAPs) in response to stimulation and thereafter detect stimulation thresholds. This allows the clinician to know how well a stimulation lead is placed, and/or how the lead needs to be adjusted to achieve more optimal results. As discussed above, since the lead placement for pudendal nerve stimulation is difficult, the patient's physiological feedback herein simplifies and improves the process of implanting the lead for pudendal nerve stimulation. Even for sacral nerve stimulation where landmarks are available to guide the lead placement, the present disclosure can still be used to optimize lead placement.

Another advantage of the present disclosure is that verbal or voluntary physical feedback from the patient is no longer required. In more detail, the stimulation current amplitude corresponding to the threshold in doing the CMAP sweep is typically below a level where the patient would actually "feel" it. In other words, as the stimulation threshold is reached, the patient's physiological response (CMAP) may indicate as such, but the patient himself may still subjectively feel very little to no stimulation sensation. Since each CMAP sweeping process may be completed before the stimulation current amplitude is strong enough to make the patient "feel something" (i.e., well into the saturation region in FIG. 13B), the entire CMAP sweeping process discussed above may be performed without the patient having to provide feedback (whether verbal or physical feedback) knowingly to the clinician. In other words, the patient may be fully or partially sedated and need not be lucid, which is helpful in the context of the present disclosure, since the patient often times is sedated during the lead placement. Even if the patient is fully conscious and lucid enough to provide verbal feedback or physical feedback via an electronic patient feedback tool, the fact that the patient need not participate in these activities may make the whole procedure more enjoyable for the patient.

Yet another advantage of the present disclosure is that its implementation is simple and not costly. For example, the clinician can perform electrodiagnosis (using the anal electrode device 1040 to obtain CMAPs) quickly and without requiring additional electromyography (EMG) equipment. The anal electrode device 1040 is also cheap and disposable after a single use, and thus its use does not result in significantly higher costs.

IPG Configured to Deliver Different Pulse Regimes to Different Leads for Pudendal Nerve Stimulation Conventional pulse generators may include a plurality of output channels, each of which is capable of delivering stimulation pulses having a particular stimulation waveform characteristic. Unfortunately, the channels for conventional pulse generators are not truly independent and separate. For example, these channels share the same clock and thus their corresponding stimulation waveforms all share the same frequency. Additionally, the waveforms from different output channels also share the same stimulation amplitude and pulse width.

These restrictions limit the versatility of the pulse generator, since different parts of the body (such as different organs or different types of nerves) may require treatment by different stimulation waveforms. Conventional pulse generators can only provide treatment to one organ or one type of nerve at a time.

To overcome the problems associated with conventional pulse generators, the present disclosure offers a pulse generator that can output truly separate and independent channels, where each channel is capable of outputting a stimulation waveform having different characteristics (such as stimulation frequency) from the waveforms outputted by other channels. This may be accomplished via separate clocks in some embodiments, and/or via advanced clock generation circuitry in other embodiments even if a single crystal clock is used.

Figure 17:
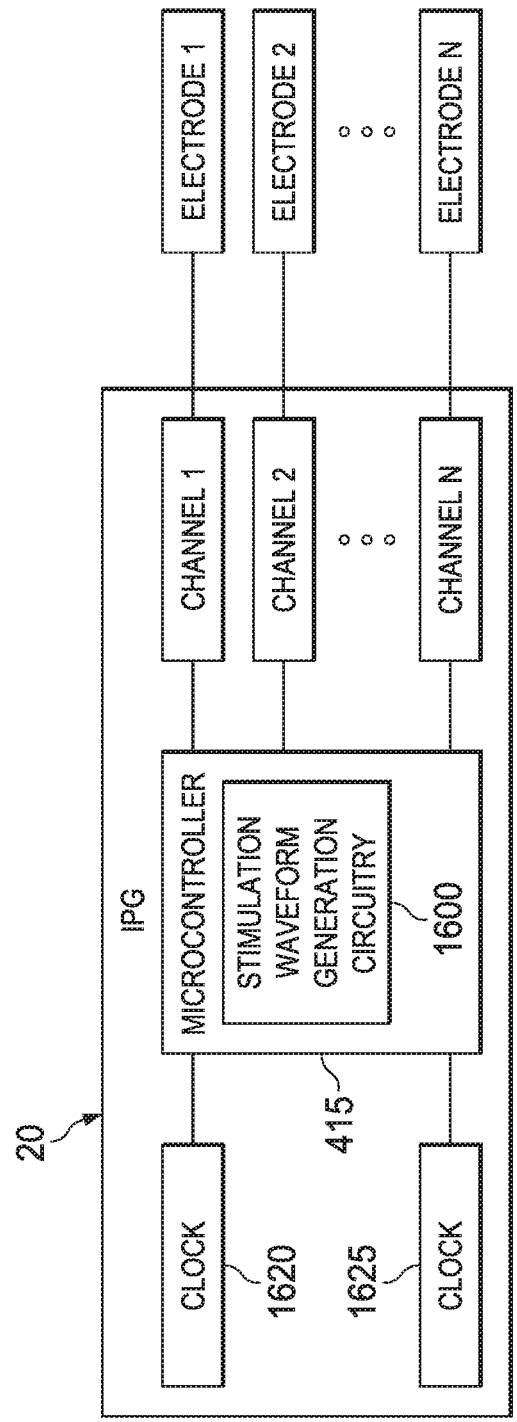
FIG. 17 is a simplified block diagram of a portion of an IPG according to embodiments of the present disclosure.

For example, referring now to FIG. 17, a simplified block diagram showing a portion of the IPG 20 is illustrated according to an embodiment of the present disclosure. As discussed above with reference to FIG. 8, the IPG 20 contains a microcontroller 415. The microcontroller 415 includes waveform generation circuitry 1600, which may include components such as amplifiers and/or digital-to-analog converters (DAC). The waveform generation circuitry generates stimulation waveforms in response to clock signals, for example clock signals received from clocks 1620 and 1625.

The clocks 1620 and 1625 may be implemented outside the microcontroller 415 in the illustrated embodiment, but they may be integrated into the microcontroller 415 in alternative embodiments. The clocks 1620 and 1625 may be crystal quartz clocks that each oscillate at a preset frequency, for example a frequency ranging from several tens of kilo-Hertz (kHz) to several tens of mega-Hertz (mHz). Alternatively, the clocks 1620 and 1625 themselves are not crystal quartz clocks, but they may receive a single clock signal generated by a crystal quartz clock (not illustrated herein) and "convert" that clock signal to different clock signals. For example, the clocks 1620 and 1625 may each include a respective phase-locked-loop (PLL). The PLL may include circuit components such as a phase detector, a charge pump, a low-pass filter, a controlled oscillator, and a frequency divider. Each PLL is designed to receive the crystal quartz clock signal having one frequency and output a frequency-locked and phase-locked signal having a different frequency. In other words, the respective PLLs in the clocks 1620 and 1625 allow each of the clocks 1620 and 1625 to provide a different clock signal having its own respective frequency.

Based on the different signals received from the clocks 1620 and 1625, the stimulation waveform generation circuitry 1600 of the microcontroller 415 generates a plurality of stimulation waveforms having different stimulation waveform characteristics. For example, the stimulation waveforms may have different frequencies. As other examples, the stimulation waveforms may have different amplitudes or pulse widths.

The IPG 20 also includes a plurality of individually-controllable output channels 1-N. Each channel is configured to output a respective one of the stimulation waveforms generated by the stimulation waveform generation circuitry. For example, each channel may include DC-blocking capacitors or diodes, stimulation drivers, current sources/sinks, and/or switches. In some embodiments, the lead wire coupled to the IPG 20 may also be considered to be a part of the channel, even though the lead wire is outside the IPG 20. The channels are described in further detail in U.S. Pat. No. 8,515,545, filed on Apr. 29, 2011, and issued on Aug. 20, 2014, the disclosure of which is hereby incorporated by reference in its entirety. The channels 1-N are electrically coupled to their respective electrode contacts on a lead, for example electrode contacts 1-N illustrated herein. Accordingly, multiple channels can each output a unique stimulation waveform to their respective electrode contacts, which can then deliver these waveforms to different body organs or different types of nerves to treat different symptoms.

In more detail, in pelvic stimulation, different organs or types of nerves react or respond to different stimulation waveforms. In other words, different types of stimulation waveforms are needed to treat different conditions. For example, a bladder may start to contract in response to a stimulation waveform of about 30 pulses/second, but it may begin to relax with about 3-5 pulses/second. As another example, a stimulation waveform needed to treat problems associated with the bladder may be different than a stimulation waveform needed to treat problems associated with the urethra. Thus, according to the various aspects of the present disclosure, it may be advantageous and desirable to stimulate a first body organ or first type of nerve with a first stimulation waveform, while a second body organ or second type of nerve is stimulated with a second stimulation waveform. As non-limiting examples, the different types of organs may include bladder, urethra, anus, etc., and the different types of nerves may include sacral nerves, pudendal nerves, and sacral spinal nerves.

In some embodiments, the different stimulation waveforms may be applied/delivered simultaneously. In other embodiments, the different types of stimulation waveforms may be applied/delivered sequentially from one channel to another channel, but from the patient's perspective, it is as if the stimulation waveforms are delivered simultaneously, because the patient cannot perceive the momentary cessation of the stimulation. Stated differently, a first stimulation waveform may be delivered (via a first channel) to a first type of nerve for one or more cycles, and then while it is paused, a second stimulation waveform may be delivered (via a second channel) to a second type of nerve for one or more cycles, and then it is paused while the first stimulation waveform is delivered again. The cycles are short enough (i.e., on the order of several microseconds or tens or hundreds of microseconds) such that it creates a therapeutic effect from the patient's perspective as if both types of nerves are being treated at the same time.

FIGS. 18A-18C illustrate simplified example stimulation waveforms according to various embodiments of the present disclosure. In FIG. 18A, two different stimulation waveforms are graphed over time. The stimulation waveform 1 may be a stimulation waveform to be delivered via a first channel to treat a first symptom in a first body region of the patient (i.e., by targeting a first nerve), and the stimulation waveform 2 may be a stimulation waveform to be delivered via a second channel to treat a second symptom in a second body region of the patient (i.e., by targeting a second nerve). In the example shown, the waveform 1 may include a burst of several square wave pulses followed by a dormant period, and it repeats again. The waveform 2 may include a burst of pulses that are a mixture of a square wave and a triangular wave, followed by a dormant period, and it repeats again. It can be seen that waveforms 1 and 2 have different waveform characteristics including waveform shape, frequency, amplitude, or pulse width. Again, the waveform 1 may be better suited to treat a first symptom of a first organ, while the waveform 2 may be better suited to treat a second symptom of a second organ.

According to various aspects of the present disclosure, the stimulation waveform for a given channel may also be a superimposition of multiple types of waveforms. Two simplified examples of the waveform superimposition are illustrated in FIGS. 18B-18C. In more detail, the waveform illustrated in FIG. 18B is a superimposition of a square wave having a lower amplitude and a higher frequency superimposed over a different square wave having a higher amplitude and a lower frequency. The waveform illustrated in FIG. 18C is a superimposition of a square wave having a lower amplitude and a higher frequency superimposed over a sine wave having a higher amplitude and a lower frequency. One benefit of the superimposition of waveforms is that patients often times respond better to the superimposed waveforms than non-superimposed waveforms. In the examples shown in FIGS. 18B and 18C, the patients may respond better to the superimposed waveforms shown in FIGS. 18B and 18C than to a square wave alone or a sine wave alone.

In addition to generating different stimulation waveforms with different waveform characteristics that can be outputted through truly separate and independent channels (e.g., by outputting their own unique stimulation waveforms), the present disclosure also utilizes a unique addressing scheme to deliver each of the stimulation waveforms to a selected one of a plurality of electrodes, where the number of electrodes far exceeds the number of channels. In more detail, one drawback of conventional pulse generators is that they have a one-to-one correspondence between its output channels and the electrode contacts on a stimulation lead. As such, to fully address a stimulation lead having X number of electrode contacts, a conventional pulse generator needs to have X number of output channels. This is a problem when the number of electrode contacts becomes large. For example, a mesh electrode array may have 256 electrode contacts in order to provide comprehensive coverage for a target stimulation region of the patient. Most conventional pulse generators are not capable of producing 256 output channels, and even if they could, it would be very expensive and messy to actually connect all 256 channels to their respective electrode contacts. To overcome this problem, the present disclosure allows a large number of electrode contacts to be addressed using a limited number of channels.

Figure 19:
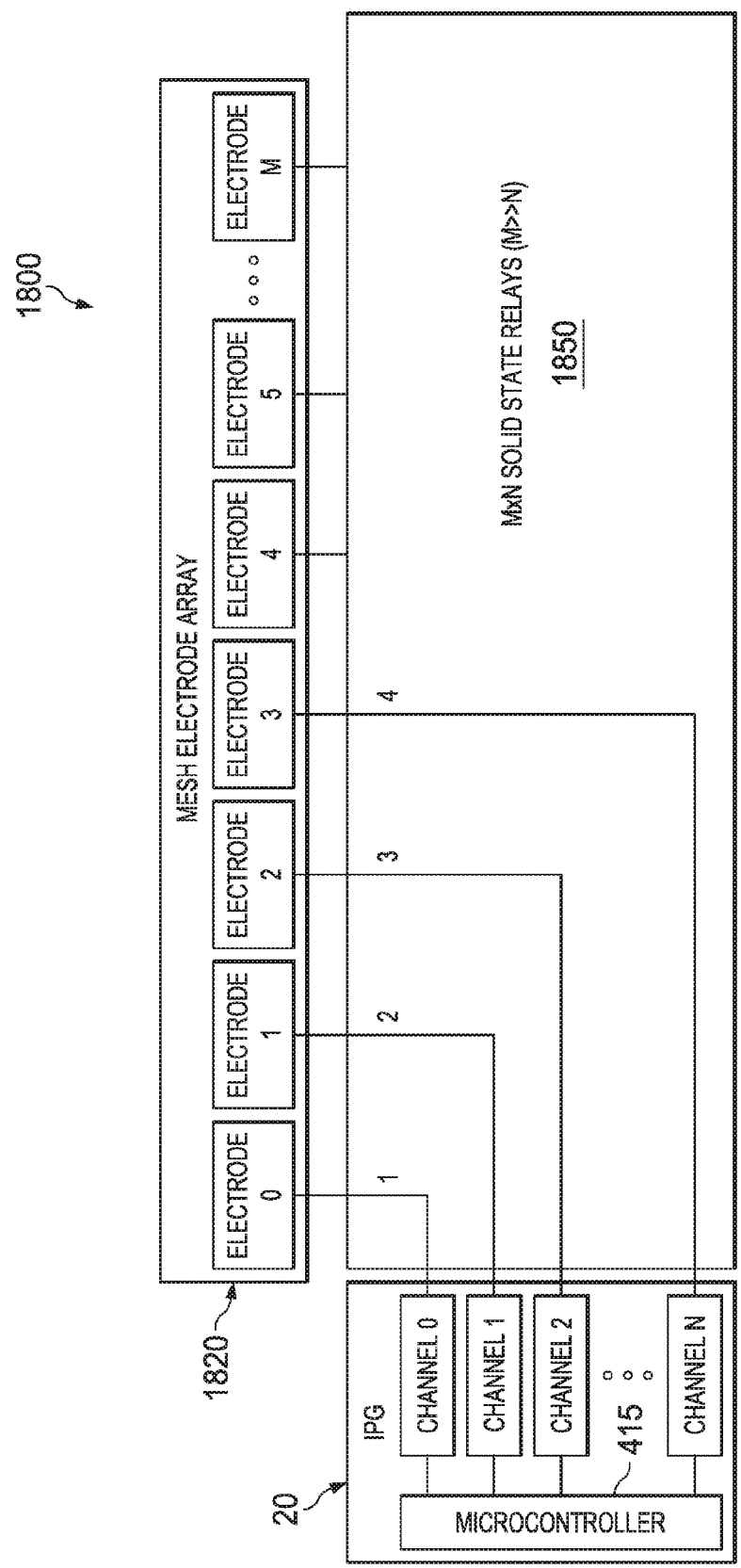
FIGS. 19-20 and 23-24 are block diagrams of various embodiments of a medical system in which a limited number of channels are used to address a far greater number of electrodes according to various aspects of the present disclosure.

For example, FIG. 19 illustrates a medical system 1800 that utilizes an example addressing scheme according to the various aspects of the present disclosure. The medical system 1800 includes an IPG, for example the IPG 20 discussed above with reference to FIGS. 2B, 8, and 17. The IPG includes an N number of output channels, each one of which is capable of outputting a unique stimulation waveform as discussed above. In the embodiment shown in FIG. 19, N=4, but it is understood that N may be any number from 1 to 32 in various embodiments.

The medical system 1800 includes a mesh electrode array 1820. The mesh electrode array 1820 includes an M number of electrodes, where M is far greater than N, for example M may be at least several times, or tens of times, or hundreds of times greater than N. In some embodiments, the mesh electrode array 1820 may be a 10×10 electrode array (having 100 electrodes) or a 16 by 16 electrode array (having 256 electrodes). In some other embodiments, the mesh electrode array 1820 may have several hundreds or thousands of electrodes.

Having such a great number of electrodes allows the mesh electrode array to provide a relatively comprehensive coverage area for the target stimulation site. Practically though, only one (or just a few) electrodes is needed to provide satisfactory stimulation for the target nerve. However, finding the ideal target nerve location to apply stimulation is not easy. Therefore, having a large number of electrodes to cover as many stimulation sites as possible will increase the likelihood that at least one of these electrodes will be located close enough to the target stimulation spot.

Conventionally, manufacturers have attempted to create an IPG that has as many output channels as possible to interoperate with the large number of electrodes. For example, if a stimulation lead with 32 electrodes is used, then the corresponding IPG used will have 32 channels, where each channel corresponds to a respective one of the electrodes on the lead. In other words, the electrodes and the stimulation channels traditionally have a one-to-one correspondence. As the number of electrodes grows, this conventional solution becomes not only wasteful (e.g., for the IPG to have so many output channels when only a few may actually be needed or used) but also impractical. For example, a large and complex connector block may be needed to route all the channels to their respective electrodes, and the routing of so many channels to their electrodes may also become very messy.

Here, the medical system 1800 utilizes a relay 1850 to electrically couple the IPG 20 and the mesh electrode array 1820 together. In the illustrated embodiment, the relay 1850 may include an M×N solid state relay, but it is understood that other types of relays may be used in alternative embodiments. The relay 1850 may include a plurality of controllable switches that can be turned on or off based on instructions received from the microcontroller of the IPG 20. The switches (e.g., a FET transistor switch), when turned on, establish electrical connections between their respective channels and the electrodes of the mesh electrode array 1820. Therefore, through the relay 1850, each of the channels of the IPG 20 is routed to (and electrically coupled to) a respective one of the electrodes on the mesh electrode array 1820, but since M is substantially greater than N (i.e., far more electrodes than channels), there is no one-to-one correspondence between the channels of the IPG 20 and the electrodes in the mesh electrode array 1820. Instead, the IPG 20 (e.g., the microcontroller component 415 inside the IPG) may instruct the relay 1850 to route or address each of the channels to any given electrode of the mesh electrode array 1820.

In the embodiment shown in FIG. 19, channel 0 of the IPG 20 is routed or addressed to electrode 0 of the mesh electrode array 1820, channel 1 of the IPG 20 is routed or addressed to electrode 1 of the mesh electrode array 1820, channel 2 of the IPG 20 is routed or addressed to electrode 2 of the mesh electrode array 1820, and channel N of the IPG 20 is routed or addressed to electrode 3 of the mesh electrode array 1820. The routing or addressing of the channels of the IPG 20 corresponds to a first point in time.

Figure 20:
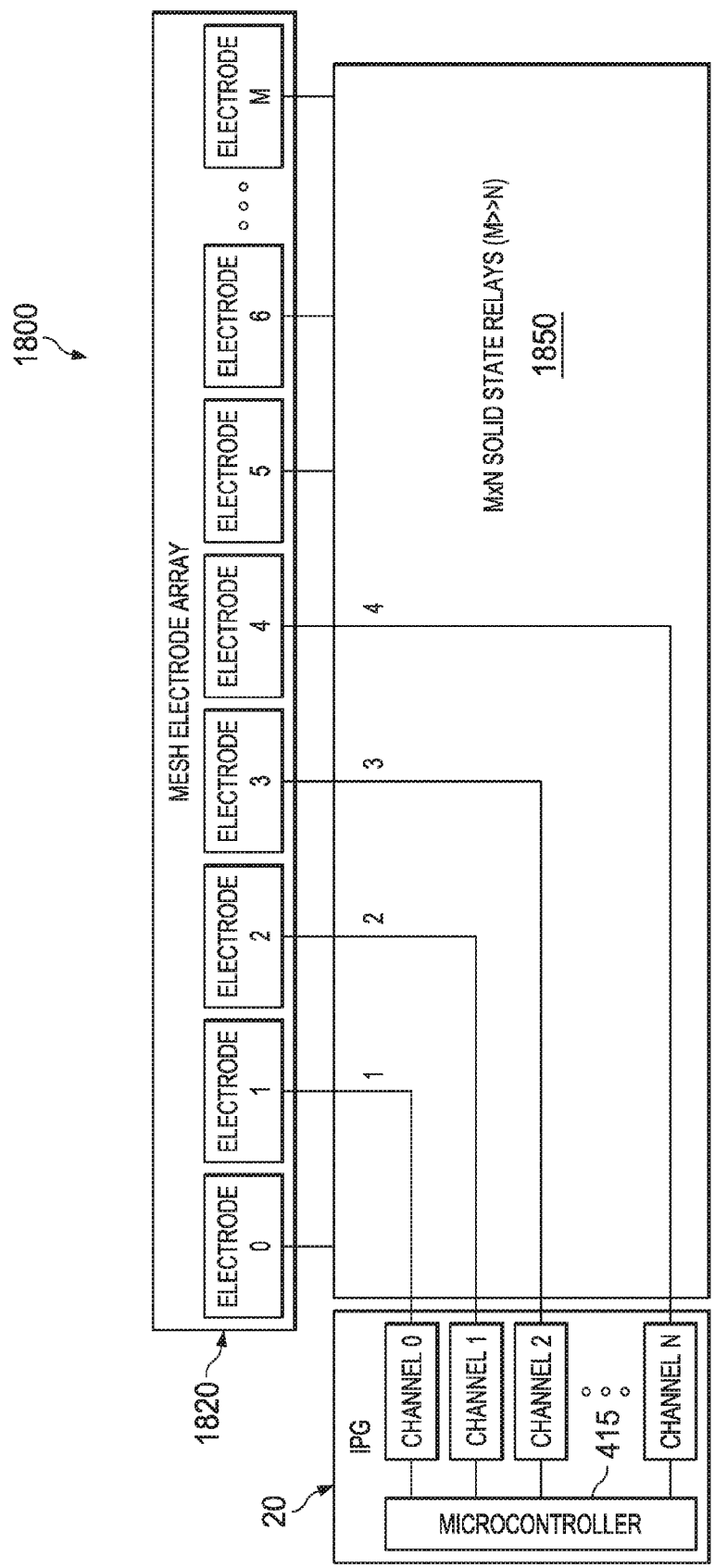

FIG. 20 shows the addressing of the channels of the IPG 20 at a second point in time that is different from the first point in time. Referring to FIG. 20, channel 0 of the IPG 20 is routed or addressed to electrode 1 of the mesh electrode array 1820, channel 1 of the IPG 20 is routed or addressed to electrode 2 of the mesh electrode array 1820, channel 2 of the IPG 20 is routed or addressed to electrode 3 of the mesh electrode array 1820, and channel N of the IPG 20 is routed or addressed to electrode 4 of the mesh electrode array 1820.

Of course, at other points in time, the channels of the IPG 20 may be routed or addressed to other electrodes of the mesh electrode array 1820, based on instructions from the microcontroller 415. As such, the medical system 1800 effectively allows a limited number of channels to have complete access to a very large number of electrodes. In addition to reducing complexity and saving costs, being able to address a large number of electrodes with a limited number of channels also allows stimulation field shaping.

Figure 21:
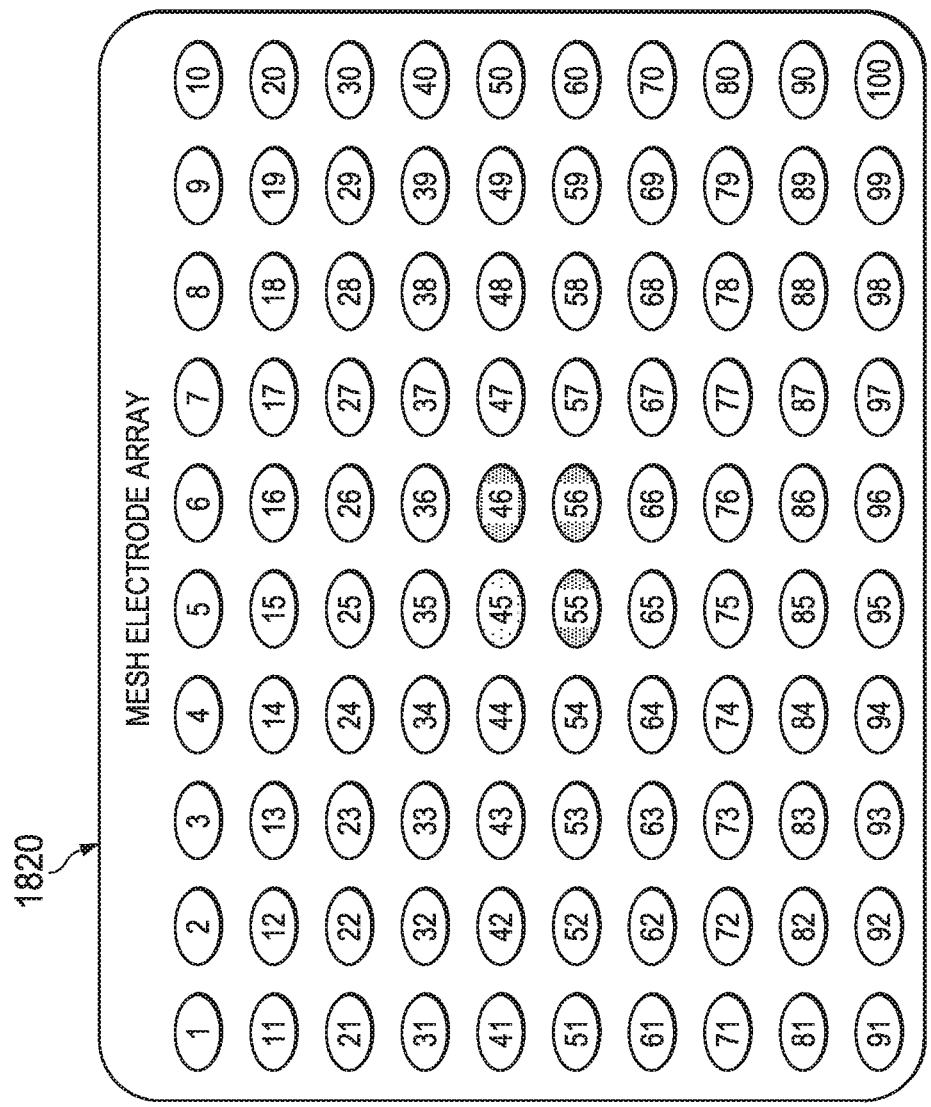
FIGS. 21-22 are a planar view of a mesh electrode array according to embodiments of the present disclosure.

In more detail, referring now to FIG. 21, a simplified planar view of an example embodiment of the mesh electrode array 1820 is illustrated. The mesh electrode array 1820 is a 10×10 array and includes 100 electrodes 1-100. As discussed above, the IPG 20 in this example only includes 4 output channels. As shown in FIG. 21, suppose that the channels 1 to 4 are electrically routed/addressed to electrodes 45, 46, 55, and 56, respectively. This is done by the relay 1850 switching on the respective switches based on commands from the microcontroller 415. Also as discussed above, since each of the channels is capable of outputting a waveform with a unique waveform characteristic such as stimulation frequency, suppose that the channel 1 is outputting a first waveform with a first stimulation frequency to electrode 45, and channels 2, 3, 4 are each outputting a second waveform with a second stimulation frequency to electrodes 46, 55, and 56. This occurs at a first point in time.

Figure 22:
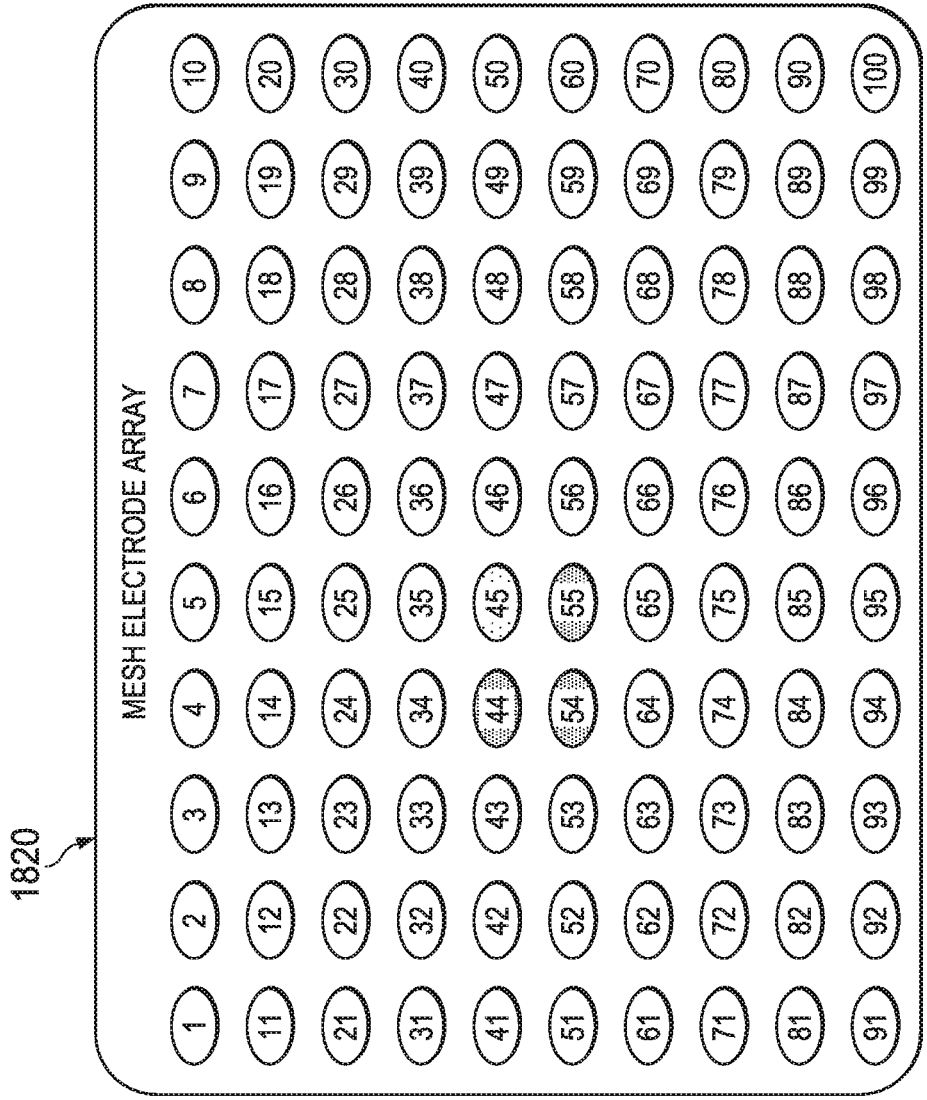

Referring now to FIG. 22, at a second point in time, the channels 1 to 4 are now electrically routed/addressed to electrodes 45, 55, 44, and 54, respectively. Again, this may be done by enabling the correct switches of the relay 1850. Channel 1 is still outputting the first waveform with the first stimulation frequency to electrode 45, but channels 2, 3, 4 are now each outputting the second waveform with the second stimulation frequency to electrodes 55, 44, and 54, respectively. Although not illustrated for reasons of simplicity, it is understood that at different points in time, the electrodes 34, 35, and 36 may also be selectively activated to deliver the second stimulation waveform. In other words, the electrodes may be turned on at different points in time to circle around the "center" electrode 45 in this example.

The activation of different electrodes at different points in time may create different stimulation fields. Specifically, at different points in time, different stimulation fields may be created by selectively switching on a subset of the switches of the relay 1850 in order to route/address desired stimulation forms from channels 1-4 to their corresponding electrodes, which may be any of the electrodes 1-100. Given such a large number of possible permutations regarding which electrodes 1-100 can be activated, and with or without differing stimulation waveforms being delivered by the activated electrodes, a great variety of stimulation fields may be created, which enhances the versatility and flexibility of the medical system 1800 in providing a satisfactory treatment therapy for a patient.

Figure 23:
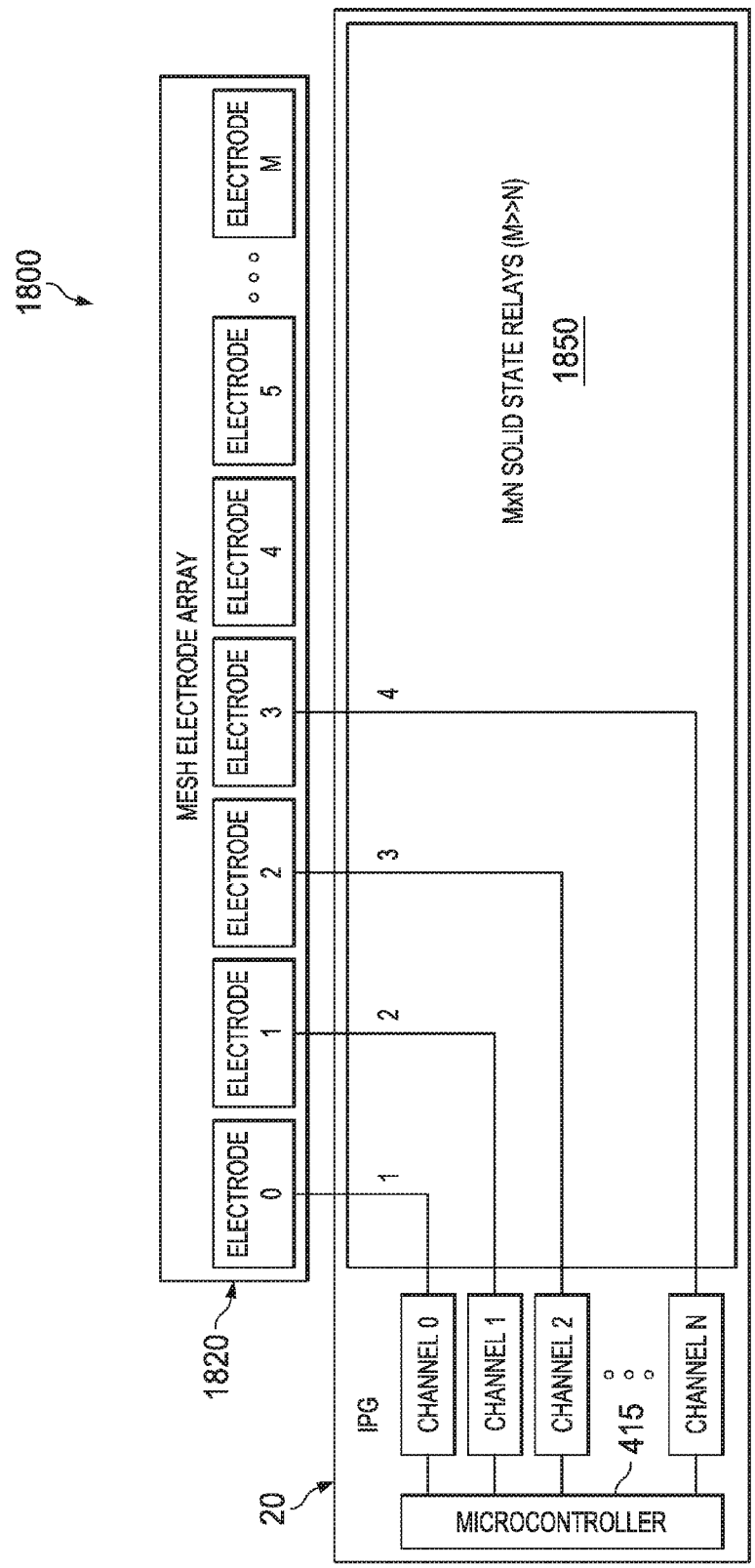
Figure 24:
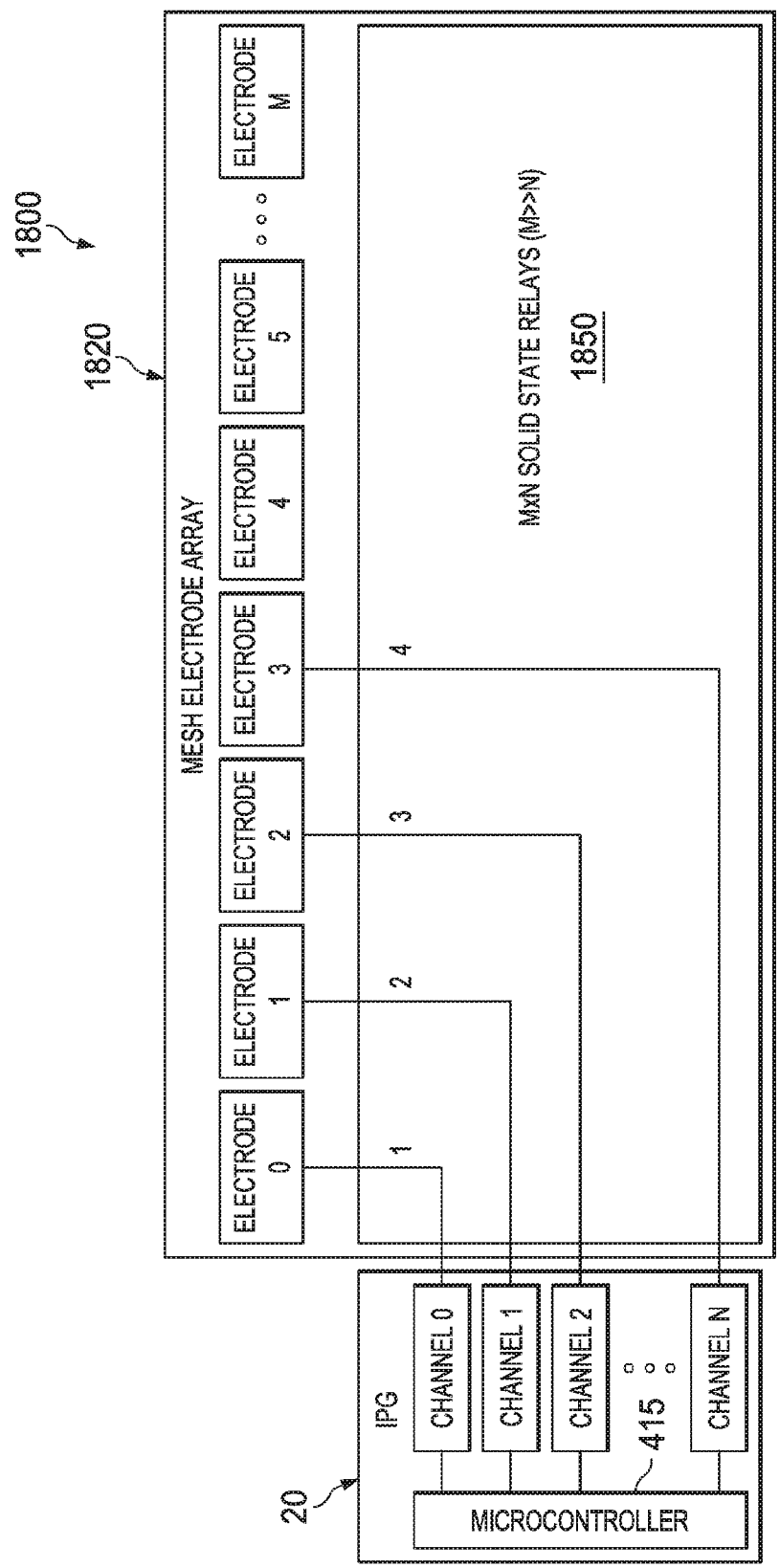

In the embodiments discussed above, the relay 1850 is implemented as a separate component from the IPG 20. For example, the relay 1850 may be implemented as a separate chip. However, it is understood that the relay 1850 may also be implemented as a part of the IPG 20, such as shown in the embodiment of FIG. 23, or even as a part of the mesh electrode array 1820 (or the stimulation lead containing the mesh electrode array 1820), such as shown in the embodiment of FIG. 24.

Figure 25:
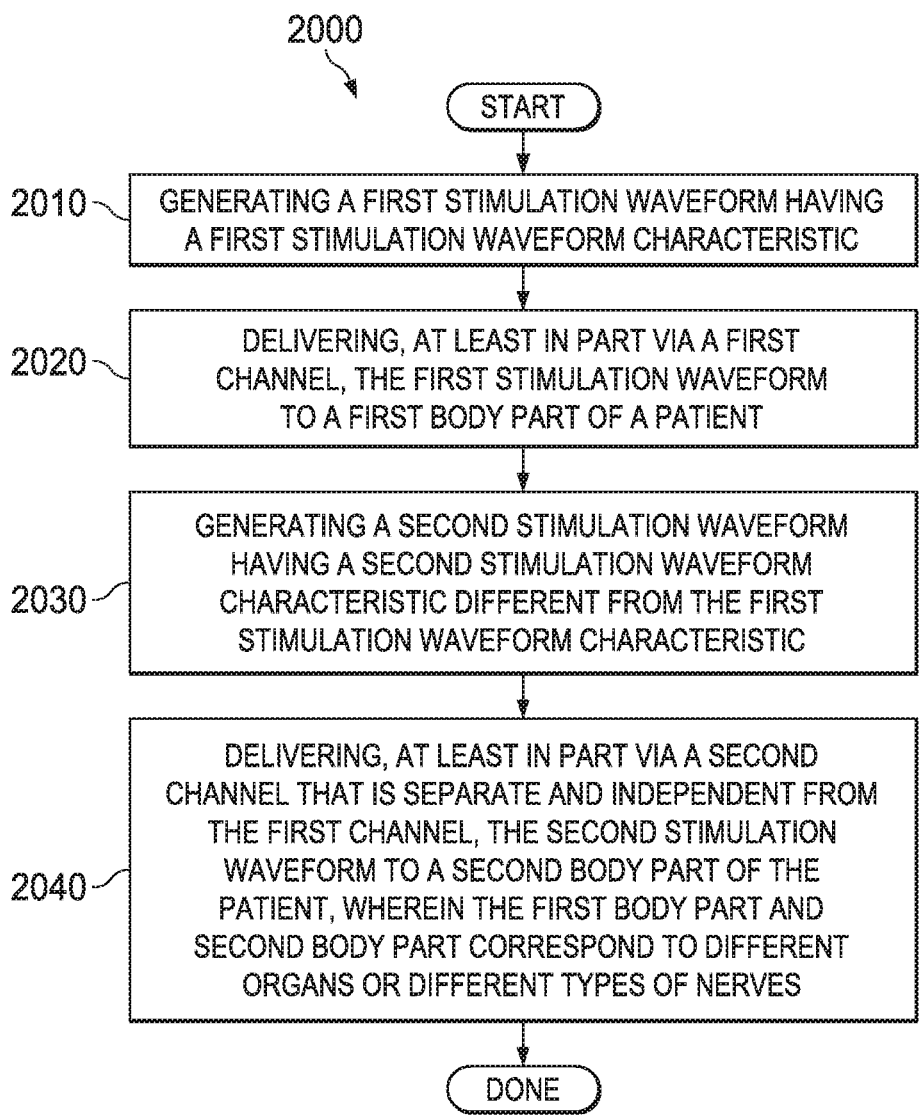
FIG. 25 is a flowchart of a method of outputting different stimulation waveforms according to embodiments of the present disclosure.

FIG. 25 is a flowchart illustrating of a method 2000 of generating different stimulation waveforms as a part of sacral nerve stimulation therapy according to various aspects of the present disclosure. The method includes a step 2010 of generating a first stimulation waveform having a first stimulation waveform characteristic.

The method includes a step 2020 of delivering, at least in part via a first channel, the first stimulation waveform to a first body part of a patient.

The method includes a step 2030 of generating a second stimulation waveform having a second stimulation waveform characteristic different from the first stimulation waveform characteristic. In some embodiments, the first stimulation waveform and the second stimulation waveform have different frequencies. For example, in some embodiments, the first stimulation waveform is generated by a first clock, and the second stimulation waveform is generated by a second clock different from the first clock. In some embodiments, the first clock and the second clock are different crystal clocks. In some embodiments, the first stimulation waveform and the second stimulation waveform have different pulse widths or amplitudes.

The method includes a step 2040 of delivering, at least in part via a second channel that is separate and independent from the first channel, the second stimulation waveform to a second body part of the patient. The first body part and second body part correspond to different organs or different types of nerves. In some embodiments, the first body part includes a sacral nerve, and the second body part includes a pudendal nerve. In such embodiments, the step 2020 of delivering of the first stimulation waveform comprises delivering the first stimulation waveform to the sacral nerve, and the step 2040 of delivering of the second stimulation waveform comprises delivering the second stimulation waveform to a pudendal nerve of the patient.

In some embodiments, at least one of the first stimulation waveform and the second stimulation waveform includes a superimposition of two or more distinct waveforms.

In some embodiments, the first stimulation waveform and the second stimulation waveform are generated by a pulse generator, such as by the stimulation waveform generation circuitry inside an IPG. The pulse generator has an N number of output channels including the first and second channels. Meanwhile, the first stimulation waveform and the second stimulation waveform are delivered via a mesh electrode array that is electrically coupled to the output channels of the pulse generator. The mesh electrode array contains an M number of electrodes. M is greater than N. In some embodiments, M is substantially greater than N, such as being multiple times greater than N. For example, N may be in a range from 1 to 16, and M may be in a range from 50 to several hundred.

It is understood that the method 2000 may include additional steps that may be performed before, during, or after the steps 2010-2040 discussed above. For example, the method 2000 may include a step of routing the first channel to a first electrode on the mesh electrode array at a first point in time, a step of routing the first channel to a second electrode on the mesh electrode array at a second point in time. The first and second electrodes are different, and the first and second points in time are different. For reasons of simplicity, other additional steps are not discussed herein in detail The present devices, systems, and methods described herein include various advantages. It is understood, however, that not all advantages are necessarily discussed herein, different embodiments may offer different advantages, and no particular advantage is required for all embodiments. One advantage is that the pulse generator is capable of outputting different stimulation waveforms via truly separate and independent channels to treat different symptoms associated with different organs. Another advantage is that being to address a large number of electrodes with limited channels simplifies the IPG design and reduces costs, while not sacrificing the flexibility of versatility of the pulse generator.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method, comprising:
applying an electrical stimulation to a patient through an electrode contact on a lead;
receiving a determination as to whether the patient, in response to the electrical stimulation, exhibited a bellows response or a toes response;
increasing a stimulation parameter of the electrical stimulation in response to a determination that the patient did not exhibit the bellows response or the toes response;
repeating the applying, the receiving, and the increasing one or more times until an earliest occurrence of: the patient exhibiting the bellows response, the patient exhibiting the toes response, the patient reporting a discomfort in response to the electrical stimulation, and a predefined upper limit of the stimulation parameter being reached; and
determining, based on the earliest occurrence of the bellows response, the toes response, the patient reporting the discomfort, and the predefined upper limit of the stimulation parameter being reached, whether the electrode contact is suitable to be used as a part of an electrical stimulation therapy for treating the patient.

2. The method of claim 1, wherein the patient exhibited the bellows response, and wherein the bellows response comprises a sensation perceived by the patient in a bellows area of the patient.

3. The method of claim 2, wherein the bellows response comprises a contraction in an anal region of the patient.

4. The method of claim 1, wherein the patient exhibited the toes response and wherein the toes response comprises a sensation perceived by the patient in a toe of the patient.

5. The method of claim 4, wherein the toes response comprises an involuntary movement of the toe of the patient.

6. The method of claim 1, further comprising: determining whether the patient felt pain in response to the electrical stimulation, and wherein the increasing the stimulation parameter is performed only if the patient did not feel pain in response to the electrical stimulation.

7. The method of claim 1, wherein the increasing the stimulation parameter comprises increasing a stimulation amplitude.

8. The method of claim 1, wherein the determining comprises:
deeming the electrode contact suitable for treating the patient if the patient exhibited the bellows response or the toes response before an occurrence of: the patient, reporting the discomfort, or the predefined upper limit of the stimulation parameter being reached; and
deeming the electrode contact unsuitable for treating the patient if the patient has not exhibited the bellows response or the toes response before an occurrence of: the patient reporting the discomfort, or the predefined upper limit of the stimulation parameter being reached.

9. The method of claim 8, further comprising:
determining, after the patient has exhibited both the bellows response and the toes response, whether the bellows response occurred before the toes response;
wherein the deeming the electrode contact suitable for treating the patient comprises deeming the electrode contact suitable for treating the patient only if the patient exhibited the bellows response before the toes response.

10. The method of claim 1, wherein the lead contains a plurality of electrode contacts, and wherein the repeating, the applying, the receiving, and the increasing one or more times, and the determining are repeated for more than one of the plurality of electrode contacts.

11. The method of claim 1, wherein the electrical stimulation therapy comprises a sacral nerve stimulation therapy.

12. A method, comprising:
applying an electrical stimulation to a patient through an electrode contact on a lead;
receiving a determination as to whether the patient, in response to the electrical stimulation, exhibited a toes response; and
increasing a stimulation parameter of the electrical stimulation in response to a determination that the patient did not exhibit the toes response;
receiving a determination as to whether the patient, in response to the electrical stimulation, exhibited a bellows response; and
increasing a stimulation parameter of the electrical stimulation in response to a determination that the patient has not yet exhibited both the toes response and the bellows response;
receiving a determination that the patient has exhibited both the bellows response and the toes response;
determining a timing of the exhibited bellows response relative to the exhibited toes response; and
determining, based on the timing of the exhibited bellows response relative to the exhibited toes response, whether the electrode contact is suitable to be used as a part of an electrical stimulation therapy for treating the patient.

13. The method of claim 12, wherein the toes response comprises an involuntary movement of one or more toes of the patient.

14. The method of claim 12, wherein the electrical stimulation therapy comprises a sacral nerve stimulation therapy.

15. The method of claim 12, wherein the bellows response comprises a contraction in an anal region of the patient.

16. A method, comprising:
applying an electrical stimulation to a patient through an electrode contact on a lead;
receiving a determination as to whether the patient, in response to the electrical stimulation, has exhibited both a bellows response and a toes response;
increasing a stimulation parameter of the electrical stimulation in response to a determination that the patient has not exhibited both the bellows response and the toes response;
determining, in response to a determination that the patient has exhibited both the bellows response and the toes response, a chronological order of the exhibited bellows response and the exhibited toes response; and
determining, based on the chronological order, whether the electrode contact is suitable to be used as a part of an electrical stimulation therapy for treating the patient.

17. The method of claim 16, wherein:
the bellows response comprises a contraction in an anal region of the patient; and
the toes response comprises an involuntary movement of the toe of the patient.

18. The method of claim 16, determining that the electrode contact is unsuitable to be used as a part of an electrical stimulation therapy for treating the patient when the patient exhibited the bellows response after the toes response.

19. The method of claim 16, further comprising: determining whether the patient felt discomfort in response to the applied electrical stimulation, and wherein the increasing the stimulation parameter is performed in response to the patient not feeling the discomfort in response to the electrical stimulation.

20. The method of claim 16, wherein the electrical stimulation therapy comprises a sacral nerve stimulation therapy.

* * * * *

UNITED STATES PATENT AND TRADEMARK OFFICE
CERTIFICATE OF CORRECTION

PATENT NO.        : 9,895,532 B2
APPLICATION NO.   : 15/229003
DATED             : February 20, 2018
INVENTOR(S)       : Norbert Kaula and Yohannes Iyassu It is certified that error appears in the above-identified patent and that said Letters Patent is hereby corrected as shown below:

In the Specification

Column 6, Lines 41-42 delete "neuro stimulation" and insert --neurostimulation--.

Signed and Sealed this
Eighth Day of May, 2018

Andrei Iancu
*Director of the United States Patent and Trademark Office*